US007060733B2

(12) United States Patent
Pandol et al.

(10) Patent No.: US 7,060,733 B2
(45) Date of Patent: Jun. 13, 2006

(54) METHODS FOR TREATING PANCREATITIS WITH CURCUMIN COMPOUNDS AND INHIBITORS OF REACTIVE OXYGEN SPECIES

(75) Inventors: Stephen J. Pandol, Los Angeles, CA (US); Ilya Y. Gukovsky, Agoura Hills, CA (US)

(73) Assignees: The Regents of the University of California, Oakland, CA (US); The United States of America as represented by the Department of Veterans' Affairs, Washington, DC (US)

( * ) Notice: Subject to any disclaimer, the term of this patent is extended or adjusted under 35 U.S.C. 154(b) by 467 days.

(21) Appl. No.: 10/218,518

(22) Filed: Aug. 15, 2002

(65) Prior Publication Data

US 2004/0037902 A1 Feb. 26, 2004

(51) Int. Cl.
*A61K 31/05* (2006.01)
(52) U.S. Cl. ...................................... 514/731; 424/756
(58) Field of Classification Search ................ 514/731, 514/886
See application file for complete search history.

(56) References Cited

U.S. PATENT DOCUMENTS 5,401,777 A * 3/1995 Ammon et al. ............. 514/731

OTHER PUBLICATIONS

Lee, J-I, et al. 1998. Nuclear factor kappa B: important transcription factor and therapeutic target. J Clin Pharmacol 38: 981-993.*
Surh, Y-J, et al. 2001. Molecular mechanisms underlying chemoprotective activities of anti-inflammatory phytochemicals: downregulation of COX-2 and iNOS through suppression of NF-kB activation. Mut. Res. 480-481: 243-268.*
Sakurada, S, et al. 1996. Induction of cytokines and ICAM-1 by proinflammatory cytokines in primary rheumatoid synovial fibroblast and inhibition by N-acetyl-L-cysteine and aspirin. Int. Immunol. 8: 1483-1493.*
Catella-Lawson, F, et al. 2001. Cyclooxygenase inhibition and thrombogenicity. Am J Med 110: 28S-32S.*
Gukovsky, I, et al. 1998. Early NF-kB activation is associated with hormone-induced pancreatitis. Am J Physiol 247: G1402-1414.*
Bagshawe, K. (1995) "Antibody-Directed Enzyme Prodrug Therapy: A Review" Drug Development Research, 34:220-230.
Topazian, M. and Gorelick, F. "Acute Pancreatitis" Pathophysiology, Chapter 93, pp. 2121-2150. No Pub Date.
Owyang, C. "Chronic Pancreatitits" Etiology, Chapter 94, pp. 2151-2177. No Pub Date.

Pandol, S., et al. (1999) "Ethanol Diet Incsreases the Sensitivity of Rats to Pancreatitis Induced by Cholecystokinin Octapeptide" Gastroenterology, 117:706-716.
Vaquero, E., et al. (2001) "Localized Pancreatic NF-κB Activation and Inflammatroy Response in Taurocholate-induced Pancreatitis" Am J. Physiol Gastrointest Liver Physiol., 280:G1197-G1208.
Vaquero, E. et al. (1999) "Myofibroblast Proliferation, Fibrosis, and Defective Pancreatic repair Induced by Cyclosporin in Rats" Gut, 45:269-277.
Bhatia, M., et al. (1999) "Inflammatory Mediators in Acute Pancreatitis" Journal of Pathology, 190:117-125.
Norman, J. (1998) "The Role of cytokines in the Pathogenesisi of Acute Pancreatitis" The American Journal of Surgery, 175:76-83.
Schmid, R and Adler, G. (1998) "Cytokines in Acute Pancratitis—New Pathophysiological Concepts Evolve" European Journal of Gastroenterology & Hepatology, 11(2):125-127.
Gukovsky, I. et al. (1998) "Early NF-κB Activation is Associated With Hormone-induced Pancreatitis" American J. Physiol., 275:G1402-G1414.
Blinman, T., et al. (2000) "Activation of Pancreatic Acinar Cells on Isolation From Tissue: Cytokine Upregulation Via p38 MAP Kinase" Am J. Physiol Cell Physiol, 279:C1993-C2003.
Frossard, J., et al. (1999) "The Role of Intercellular Adhesion Molecule 1 and Neutrophils in Acute Pancreatitis and Pancreatitis-Associated Lung Injury" Gastroenterology, 116:694-701.
Gukovskaya, A., et al. (1997) "Pancreatic Acinar Cells Produce, Release, and Respond to Tumor Necrosis Factor-α Role in Regulating Cell Death and Pancreatitis" Journal of Clinical Investigation, 100(7):1853-1862.
Han, B. and Logsdon, C. (1999) "Cholecystikinin Induction of *mob-l* Chemokine Expression in Pancreatic Acinar Cells Requires NF-κB Activation" American J. Physiol. 277:C74-C82.

(Continued)

*Primary Examiner*—Sandra E. Saucer
*Assistant Examiner*—Lora E Barnhart
(74) *Attorney, Agent, or Firm*—Suzannah K. Sundby, Esq.; Smith, Gambrell & Russell, LLP

(57) ABSTRACT

Disclosed are methods of treating, preventing, modulating, attenuating, or inhibiting a disease or a disorder associated with inflammation related to NF-κB activation in a subject which comprises administering to the subject at least one curcumin compound. Also disclosed are combination therapies comprising the administration of at least one curcumin compound and at least one ROS inhibitor. Pharmaceutical compositions and kits are also disclosed.

19 Claims, 5 Drawing Sheets

OTHER PUBLICATIONS

Zaninovic, V., et al. (2000) "Cerulein Upregulated ICAM-1 in Pancreatic Acinar Cells, Which Mediates Neutrophil Adhesion to These Cells" Am J Physiol Gastrointest Liver Physiol, 279:G666-G676.

Sandoval D., et al. (1996) "the Role of Neutrophils and Platelet-Activating Factor in Mediating Experimental Pancreatitis" Gastroenterology, 111:1081-1091.

Tartaglia, L. and Goeddel, D. (1992) "Two TNF Receptors" Immunology Today, 13(5):151-153.

Hohmann, H., et al. (1990) "Expression of the Types A and B Tumor Necrosis Factor (TNF) Receptors is Independently Regulated, and Both Receptors Mediate Activation of the Transcription Factor NF-κB" Journal of Biological Chemistry, 265:36: 22409-22417.

Barnes et al. (1997) "Nuclear Factor-κB—A Pivotal Transcription Factor in Chronic Inflammatory Diseases" New England Journal of Medicine, 336:15:1066-1071.

Ben-Baruch A. et al. (1995) "Signals and Receptors Involved in Recruitment of Inflammatory Cells" Journal of Biological Chemistry, 270(20):11701-11706.

Beauparlant, P. and Hiscott J. (1996) "Biological and Biochemical Inhibitors of the NF-κB/Rel Proteins and Cytokine Synthesis" Cytokine & Growth Factor Reviews, 7(2):175-190.

Van Antwerp. D., et al. (1996) "Suppression of TNF-α-Induced Apoptosis by NF- κB" Science, 274:787-789.

Wang, C., et al. (1996) "TNF-and Cancer Therapy-Induced apoptosis: Potentiation by Inhibition of NF- κB" Science, 274:784-787.

Sen, R. and Baltimore D. (1986) "Multiple Nuclear Factors Interact with the Immunoglobulin Enhancer Sequences" Cell, 46:705-716.

Verma, I., et al. (1995) "Rel/NF- κB/I κB Family: Intimate Tales of Association and Dissociation" Genes & Development, 9:2723-2735.

Wulczyn, G. (1996) "The NF- κB/Rel and I κB Gene Families: Mediators of Immune Response and Inflammation" J. Mol. Med. 74(12):749-769.

DiDonato J., et al. (1996) "Mapping of the Inducible IκB Phosphorylation Sites That Signal Its Ubiquitination and Degradation" Molecular and Cellular Biology, 16(4):1295-1304.

Flohe, L., et al. (1997) "Redox Regulation of NF-Kappa B Activation" Free Radical Biology & Medicine, 22(6):115-1126.

Schreck R. and Baeuerle P. (1994) "Assessing Oxygen Radicals as Mediators in Activation of Inducible Eukaryotic Transcription Factor NF-κB" Methods in Enzymology, 234:151-163.

Karin, M., et al. (1997) "AP-1 Function and Regulation" Current Opinion in Cell Biology, 9:240-246.

Sluss, H., et al. (1994) "Signal Transduction by Tumor Necrosis Factor Mediated by JNK Protein Kinases" Molecular and Cellular Biology, 14(12):8376-8384.

Brenner, D., et al. (1989) "Prolonged Activation of Jun and Collagenase Genes by Tumour Necrosis Factor-α" Nature, 337:661-663.

Whitmarsh and Davis (1996) "Transcription Factor AP-1 Regulation by Mitogen-Activated Protein Kinase Signal Transduction Pathways" J. Mol. Med. 74(10):589-607.

Westwick J., et al. (1994) "Tumor Necrosis Factor α Stimulates AP-1 Activity Through Prolonged Activation of the c-June Kinase" Journal of Biological Chemistry, 269:42:26369-26401.

Singh and Aggarwal (1995) "Activation of Transcription Factor NF- κB Is Suppressed by Curcumin (Diferulolylmethane)" J. Biol. Chem. 270(42):24995-25000.

Pendurthi, U., et al. (1997) "Inhibition of Tissue Factor Gene Activation in Cultured Endothelial Cells by Curcumin" Arteriosclerosis, Thrombosis, and Vascular Biology, 17:3406-3413.

Luo, Y., et al. (1999) "IntrastriatalDopamine Injection Induces Apoptosis Through Oxidation-Involved Activation of Transcription Factors AP-1 and NF- κB in Rats" Molecular Pharmacology, 56:254-264.

Soler, A. et al. (1999) "Activation of NF- κB is Necessary for the Restoration of the Barrier Function of an Epithelium Undergoing TNF-α-induced Apoptosis" European Journal of Cell Biology, 78:56-66.

Jobin, C., et al. (1999) "Curcumin Blocks Cytokine-Mediated NF- κB Activation and Proinflammatory Gene Expression by Inghibiting Inhibitory Factor I- κB Kinase Activity" J. of Immunol., 163(6):3474-3483.

Pan, M., et al. (2000) "Comparative Studies on the Suppression of Nitric Oxide Synthase by Curcumin and Its Hydrogenated Metabolites through Down-regulation of IκB Kinase and NF κB Activation in Macrophages" Biochemical Pharmacology, 60:1665-1676.

Deveraux Q. and Reed, J. (1999) "IAP Family Proteins—Suppressors of Apoptosis" Genes & Development, 13:239-252.

Wolf, B. and Green, D. (1999) "Suicidal Tendencies: Apoptotic Cell Death by Caspase Family Proteinases" Journal of Biological Chemistry, 274(29):20049-20052.

Kaiser, A. (1995) "Relationship Between Severity, Necrosis, and Apoptosis in Five Models of Experimental Acute Pancreatitis" American J. Physiol., 269:C1295-C1304.

Lee, R. et al. (1984) "New Synthetic Cluster Ligands for Galactose/N- Acetylgalactosamine-Specific Lectin of Mammalian Liver" Biochemistry, 23(18):4255-4261.

Bertolini, G., et al. (1997) "A New Rational Hypothesis for the Pharmacoophore of the Active Metabolite of Leflunomide, a Potent Immunosuppressive Drug" J. Med. Chem, 40:2011-2016.

Shan, D. et al. (1997) "Prodrug Strategies Based on Intramolecular Cyclization Reactions" Journal of Pharmaceutical Sciences, 86(7):765-767.

Bagshawe, K. (1995) "Anitbody-Directed Enzyme Prodrug Therapy: A Review" Drug Development Research, 34:220-230

Bodor, N. (1984) "Novel Approaches to the Design of Safer Drugs: Soft Drugs and Site- specific Chemical Delivery Systems" Advances in Drug Research, 13:254-331.

Bundgaard, H. (1985) "Formation of Prodrugs of Amines, Amides, Ureides, and Imides" Methods of Enzymology, 112:347-359.

Gukovskaya, A. et al. (1996) "Mechanisms of Cell Death After Pancreatic Duct Obstruction in the Opossum and the Rat" Gasteroenterology, 110:875-884.

Gukovskaya, A. et al. (2002) "Neutrophils and NADPH Oxidase Mediate Intrapancreatic Trypsin activation in Murine Experimental Acute Pancreatitis" Gasteroenterology, 111:974-984.

Kawabata, S. et al. (1987) "Highly Sensitive Peptide-4-methylcoumaryl-7-amide Substrates for Blood-Clotting Proteases and Trypsin" Eur. J. Biochem, 172:17-25.

Pandol, S. et al. (1982) "Mechanism of [Tyr$^4$] Bombesin-Induced Desensitization in Dispersed Acini from Guinea Pig Pancreas" Journal of Biological Chemistry, 257(20):12024-12029.

* cited by examiner

METHODS FOR TREATING PANCREATITIS WITH CURCUMIN COMPOUNDS AND INHIBITORS OF REACTIVE OXYGEN SPECIES

STATEMENT REGARDING FEDERALLY SPONSORED RESEARCH OR DEVELOPMENT

This invention was made with Government support by the Department of Veterans Affairs and Grant Nos. AA11199, DK41301, and DK59508, awarded by the National Institutes of Health. The Government has certain rights in this invention.

BACKGROUND OF THE INVENTION

1. Field of the Invention

The present invention generally relates to compounds, compositions, and methods for treating pancreatitis. Specifically, the present invention relates to compounds, compositions, and methods for inhibiting the key molecular pathways that mediate pancreatitis, which compounds and compositions include curcumin compounds and inhibitors of reactive oxygen species (ROS).

2. Description of the Related Art

Pancreatitis is generally divided into acute pancreatitis and chronic pancreatitis. See Topazian M, et al. (1999) "Acute Pancreatitis" TEXTBOOK OF GASTROENTEROLOGY Philadelphia: Lippincott Willimas & Wilkins, p. 2121–2150; Owyang C. (1999) "Chronic Pancreatitis" TEXTBOOK OF GASTROENTEROLOGY Philadelphia: Lippincott Willimas & Wilkins, p. 2151–2177. Acute pancreatitis is characterized by acute inflammation in the pancreas accompanied by necrosis of the parenchymal cells, i.e. acinar cells, and duct cells. The most common causes of acute pancreatitis are alcoholism and gallstone disease. Alcohol sensitizes the pancreas to the inflammatory response and inhibition of this inflammatory response results in improvement in the severity of the pancreatitis. See Pandol SJ, et al. (1999) Gastroenterology 117:706–716. Gallstones cause pancreatitis by both obstructing the pancreatic duct and causing reflux of bile into the pancreatic duct as the stones migrate from the gallbladder to the common bile duct, ampulla of Vater and duodenum. See Topazian M, et al. (1999). Bile reflux-induced pancreatitis can also be ameliorated by inhibition of the inflammatory response. See Vaquero E, et al. (2001) Am J Physiol 280:G1197–G1208. Chronic pancreatitis results from continued episodes of acute pancreatitis and is most commonly caused by ethanol abuse. See Owyang C. (1999). Development of chronic pancreatitis includes chronic inflammation as well fibrosis and loss of parenchymal tissue. See Vaquero E, et al. (1999) Gut 45:269–277.

A substantial body of evidence indicates that one of the first events in the development of pancreatitis is the initiation of an inflammatory response in the parenchymal cells of the pancreas. The pancreatic acinar cell is capable of responding to noxious stimuli by upregulating signaling systems that regulate the production of pro-inflammatory inflammatory cytokines/chemokines and other inflammatory molecules. See Pandol S J, et al. (1999) Gastroenterology 117:706–716; Vaquero E, et al. (2001); Vaquero E, et al. (1999); Bhatia M, et al. (2000) J Pathol 190:117–125; Norman J (1998) Am J Surg 175:76–83; Schmid R M, et al. (1999) Eur J Gastroenterol Hepatol 11:125–127; Gukovsky I, et al. (1998) Am J Physiol 275:G1402–G1414; Blinman T A, et al. (2000) Am J Physiol 279:C1993–C2003; Frossard J L, et al. (1999) Gastroenterology 116:694–701; Gukovskaya A S, et al. (1997) J Clin Invest 100:1853–1862; Han B, et al. (1999) Am J Physiol 277:C74–C82; and Zaninovic V, et al. (2000) Am J Physiol 279:G666–G676. The signaling systems include the activation of the transcription factors, nuclear factor-κB (NF-κB) and activating peptide-1 (AP-1), as well as p38 MAP kinase. See Blinman T A, et al. (2000). The proinflammatory cytokines/chemokines include tumor necrosis factor alpha (TNFα), interleukin-6 (IL-6), IL-8, monocyte chemotactic protein-1 (MCP-1), macrophage inflammatory protein-2 (MIP-2), and the like. Other inflammatory molecules upregulated by these signaling systems include inducible nitric oxide synthase (iNOS) and intercellular adhesion molecule-1 (ICAM-1). See Zaninovic V, et al. (2000).

Inhibition of the inflammatory signaling systems by N-acetylcysteine, an antioxidant, results in the attenuation of both the inflammatory response and parenchymal injury responses of pancreatitis. See Vaquero E, et al. (2001); and Gukovsky I, et al. (1998). That is, the inhibition results in decreased expression of cytokines/chemokines and inflammatory cell infiltration in the pancreas. In addition, the inhibition of the inflammatory response results in significant reduction in the parenchymal injury, such as necrosis of parenchymal cells and activation of digestive enzymes. See Vaquero E, et al. (2001); Gukovsky I, et al. (1998); Gukovskaya A S, et al. (1997); Zaninovic V, et al. (2000); and Sandoval D, et al. (1996) Gastroenterology 111:1081–1091. Thus, the inflammatory response represents a central event in the mechanism of pancreatitis.

Currently, there are no therapies for either acute of chronic pancreatitis that address the mechanism of the disease. See Topazian M, et al. (1999). Prior art therapies are merely supportive measures that keep patients alive during an episode of acute pancreatitis, and measures to deal with complications of the disease during both the acute and chronic stages. As a result of a lack of therapeutic strategies directed to the mechanism of pancreatitis, prior art therapies have had little effect in decreasing the morbidity and mortality due to pancreatitis.

Thus, a need still exists for compounds, compositions, and methods for treating, preventing, and inhibiting pancreatitis.

SUMMARY OF THE INVENTION

In some embodiments, the present invention relates to a method of treating, preventing, modulating, attenuating, or inhibiting a disease or a disorder associated with inflammation related to NF-κB activation in a subject which comprises administering to the subject at least one curcumin compound. In preferred embodiments, the disease or the disorder is pancreatitis, arthritis, inflammatory bowel disease, nephritis, pneumonitis, hepatitis, encephalitis, acute inflammation, or chronic inflammation. The method may further comprise administering to the subject at least one ROS inhibitor such as N-acetylcysteine, vitamins C, A and E, beta-carotene, allopurinol, carvediol, and coenzyme Q. In some embodiments, the subject is diagnosed with the disease or disorder. In preferred embodiments, the disease or disorder is pancreatitis. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

In some embodiments, the present invention provides a method of modulating or attenuating the expression of IL-6, TNFα, KC, IL-8, or iNOS in a subject comprising administering to the subject at least one curcumin compound. The method may further comprise administering to the subject at least one ROS inhibitor such as N-acetylcysteine, vitamins C, A and E, beta-carotene, allopurinol, carvediol, and coenzyme Q. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

In some embodiments, the present invention provides a method of preventing or inhibiting the amount of IκBα and IκBβ from decreasing in a subject comprising administering to the subject at least one curcumin compound. The method may further comprise administering to the subject at least one ROS inhibitor such as N-acetylcysteine, acetylcysteine, vitamins C, A and E, beta-carotene, allopurinol, carvediol, and coenzyme Q. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

In some embodiments, the present invention provides a method of preventing or inhibiting the degradation of IκBα and IκBβ in a subject comprising administering to the subject at least one curcumin compound. The method may further comprise administering to the subject at least one ROS inhibitor such as N-acetylcysteine, vitamins C, A and E, beta-carotene, allopurinol, carvediol, and coenzyme Q. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

In some embodiments, the present invention provides a method of inducing apoptosis and decreasing necrosis of pancreatic tissue in a subject comprising administering to the subject at least one curcumin compound. The method may further comprise administering to the subject at least one ROS inhibitor such as N-acetylcysteine, vitamins C, A and E, beta-carotene, allopurinol, carvediol, and coenzyme Q. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

A method of inhibiting AP-1 activation, NF-κB activation, trypsin activation, or neutrophil infiltration, in a subject comprising administering to the subject at least one curcumin compound. The method may further comprise administering to the subject at least one ROS inhibitor such as N-acetylcysteine, vitamins C, A and E, beta-carotene, allopurinol, carvediol, and coenzyme Q. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclooxygenase inhibitors, and other non-steroidal anti-inflammatory agents.

A method of activating or increasing capsase activity in a subject comprising administering to the subject at least one curcumin compound. The method may further comprise administering to the subject at least one ROS inhibitor such as N-acetylcysteine, vitamins C, A and E, beta-carotene, allopurinol, carvediol, and coenzyme Q. In some embodiments, the method further comprises administering to the subject at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

In some embodiments, the present invention provides a pharmaceutical composition comprising at least one curcumin compound and at least one ROS inhibitor and a pharmaceutically acceptable carrier. The composition may further comprise at least one ROS inhibitor such as N-acetylcysteine, vitamins C, A and E, beta-carotene, allopurinol, carvediol, and coenzyme Q. In some embodiments, the composition may further comprise at least one supplementary active compound selected from the group consisting of corticosteroids, glucocorticoids, cyclooxygenase (COX) inhibitors, analgesics, substance P inhibitors, vanilloid receptor inhibitors, cyclo-oxygenase inhibitors, and other non-steroidal anti-inflammatory agents.

In some embodiments, the present invention provides a kit comprising at least one curcumin compound packaged together with instructions for treating, preventing, modulating, attenuating, or inhibiting a disease or a disorder associated with inflammation related to NF-κB activation in a subject. The kit may further comprise at least one ROS inhibitor.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DETAILED DESCRIPTION OF THE INVENTION

Figure 1:
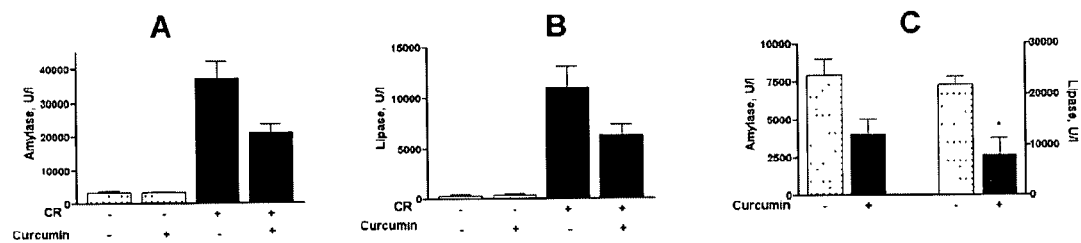
FIG. 1A shows serum amylase in control rats and rats with cerulein pancreatitis treated without curcumin (CR, −) and rats with cerulein pancreatitis treated with curcumin (CR, +). Values are means+SE from at least 4 animals for each group. * indicates that the values for animals with pancreatitis receiving curcumin were significantly lower than for those without curcumin ($p<0.05$).
FIG. 1B shows serum lipase in control rats and rats with cerulein pancreatitis treated without curcumin (CR, −) and rats with cerulein pancreatitis treated with curcumin (CR, +). Values are means+SE from at least 4 animals for each group. * indicates that the values for animals with pancreatitis receiving curcumin were significantly lower than for those without curcumin ($p<0.05$).
FIG. 1C shows serum amylase and lipase in rats with ethanol/CCK pancreatitis treated without and with curcumin. Values are means+SE from at least 4 animals for each group. * indicates that the values for animals with pancreatitis receiving curcumin were significantly lower than for those without curcumin (p<0.05).

The present invention is directed to compounds, compositions, and methods for treating, preventing, and inhibiting pancreatitis.

During pancreatitis, the inflammatory process is involved in regulating cell injury and death responses of the parenchymal cells in the pancreas. Transcription factors, NF-κB and AP-1, regulate the inflammatory process and are activated in pancreatitis. Inhibiting the activation of NF-κB and AP-1 with an inhibitor of ROS production, N-acetylcysteine, has been found to improve pancreatitis. See Vaquero E, et al. (2001); and Gukovsky I, et al. (1998).

Much of the information on nuclear factor-κB (NF-κB) comes from TNFα activation studies. Engagement of TNFα R1 activates a diverse group of intracellular signaling pathways. See Tartaglia L A, et al. (1992) Immunol Today 13:151–153; and Hohmann H P, et al. (1990) J Biol Chem 265:22409–2217. One of the main routes of TNFα-induced signaling leads to activation of the transcription factor NF-κB. See Barnes P J, et al. (1997) N Engl J Med 336:1066–1071. Activation of NF-κB is a major signal transduction pathway induced by IL-1β as well. See Barnes P J, et al. (1997).

NF-κB regulates both the expression of pro-inflammatory cytokines and apoptosis in other systems. See Tartaglia L A, et al. (1992); Hohmann H P, et al. (1990); Barnes P J, et al. (1997); Ben Baruch A, et al. (1995) J Biol Chem 270:11703–11706; Beauparlant P, et al. (1996) Cytokine Growth Factor Rev 7:175–190; Van Antwerp D J, et al. (1996) Science 274:787–789; and Wang C Y, et al. (1996) Science 274:784–787. NF-κB was first identified as a regulator of the expression of the immunoglobulin κ light-chain gene in murine B lymphocytes. See Sen R and Baltimore D (1986) Cell 46:705–716.

The activated form of NF-κB is usually a heterodimer consisting of two proteins, p65 (RelA) and p50. Several other subunits have been identified that may allow specificity in activating NF-κB target genes. See Verma I M, et al. (1995) Genes Dev 9:2723–2735; Wulczyn F G, et al. (1996) J Mol Med 74:749–769. In the unstimulated state, NF-κB is bound in the cytoplasm to inhibitory κB proteins (IκBs), IκBα and IκBβ, thereby preventing NF-κB from entering the nucleus. With stimulation, IκBs are phosphorylated thereby resulting in their transport to and rapid degradation by proteasomes. See Barnes P J, et al. (1997); Beauparlant P, et al. (1996); and DiDonato J, et al. (1996) Mol Cell Biol 16:1295–1304. With IκB degradation, NF-κB translocates into the nucleus where it binds to promoter regions of target genes. Measurements of activation of NF-κB are based on localization of the NF-κB proteins in the nucleus of the cell. See Pandol S J, et al. (1999); Vaquero E, et al. (2001); and Gukovsky I, et al. (1998).

Although the mechanisms involved in NF-κB activation and signaling pathways involved in the action of these stimuli and the role of IκB phosphorylation and degradation have not been completely elucidated, the following stimuli have been found to result in NF-κB activation in other systems: TNFα, IL-1βPAF, protein kinase C, phorbol esters, H₂O₂, and viruses. See Barnes P J, et al. (1997); and Wang C Y, et al. (1996) Science 274:784–787.

In addition to kinases involved in NF-κB activation, the oxidative state of the cell is important in regulating NF-κB activation. See Wulczyn F G, et al. (1996); Flohe L, et al. (1997) Free Radic Biol Med 22:1115–1126; and Schreck R, et al. (1994) Methods Enzymol 234:151–163. In fact, antioxidants such as N-acetylcysteine (NAC) inhibit NF-κB activation. See Beauparlant P, et al. (1996); Flohe L, et al. (1997); Schreck R, et al. (1994). How the oxidative state regulates the pathways involved in NF-κB activation is unknown.

NF-κB activation in both acute and chronic inflammatory states is important because NF-κB activation upregulates various pro-inflammatory cytokines (TNFα, IL-1β, IL-6), chemokines (IL-8, MCP-1, GRO-α), inflammatory enzymes (inducible nitric oxide synthase (iNOS), inducible cyclooxygenase-2,5-lipoxygenase, cytosolic phospholipase $A_2$) and adhesion molecules (ICAM-1, E-selectin). See Barnes P J, et al. (1997); Beauparlant P, et al. (1996); and Wulczyn F G, et al. (1996). For example, NF-κB has recently been shown to be strongly activated in pancreatitis and inhibition of NF-κB with NAC decreased intrapancreatic cytokine expression and ameliorated the disease. See Pandol S J, et al. (1999); Vaquero E, et al. (2001); and Gukovsky I, et al. (1998).

Activation protein-1 (AP-1) is another transcription factor that is activated by TNFα and IL-1β. AP-1 family of transcription factors include homodimers and heterodimers of Jun (c-Jun, JunB, JunD), Fos (c-Fos, FosB), or activating transcription factor proteins (ATF2, ATF3). See Karin M, et al. (1996) J Mol Med 74:589–607. AP-1 regulates the expression of certain cytokines and chemokines, in particular, IL-8. See Ben Baruch A, et al. (1995). AP-1 also regulates expression of metalloproteinases, such as collagenase and stromelysin, which play an important role in inflammatory diseases. See Karin M, et al. (1996).

Modulating c-Jun and c-Fos gene expression may regulate AP-1 activity. For example, TNFα has been shown to induce c-Jun gene expression. See Sluss H K, et al. (1994) Mol Cell Biol 14:8376–8384; and Brenner D A, et al. (1989) Nature 337:661–663. C-Jun transcriptional activity may be regulated by modulating its phosphorylated status. In particular, the N-terminus of c-Jun may be phosphorylated by an inducible Jun kinase (JNK), a member of the MAP kinase family. See Whitmarsh A J, et al. (1996) J Mol Med 74:589–607; and Brenner D A, et al. (1989). In most studied cell types TNFα and IL-1β activate JNK. See Whitmarsh A J, et al. (1996); and Westwick J K, et al. (1994) J Biol Chem 269:26396–26401. In some cells a weak ERK activation by TNFα also occurs. See Brenner D A, et al. (1989); and Westwick J K, et al. (1994). The biological functions of JNK pathways are yet to be understood. In most non-lymphoid cells, cytokines through MAP kinase pathways negatively regulate cell growth and induce apoptotic and necrotic cell death.

Thus, the present invention relates to compounds, compositions, and methods for treating, preventing, attenuating, or inhibiting pancreatitis by modulating NF-κB activation, AP-1 activity, or both. The compositions of the present invention include curcumin compounds. The compositions of the present invention may also include inhibitors of reactive oxygen species (ROS) such as N-acetylcysteine, vitamins C, A and E, beta-carotene, allopurinol, carvediol, coenzyme Q, and the like.

Curcumin is a naturally occurring phytochemical from the root of *Curcuma longa*, which is used to make turmeric, the spice that gives the yellow color to curry dishes. Curcumin inhibits the activation of NF-κB and AP-1 in various cell types and tissues with no effect on p38 MAP kinase. See Singh S. and Aggarwal *Bifidobacterium* (1995) J Biol Chem 270:24995–5000; Pendurthi U R, et al. (1997) Arterioscler Thromb Vasc Biol 17: 3406–3413; Luo Y, et al. (1999) Mol Pharmacol 56:254–264; Soler A P, et al. (1999) Eur J Cell Biol 78 :56–66; Jobin C, et al. (1999) J Immunol 163: 3474–3483; and Pan M H, et al. (2000) Biochem Pharmacol 60:1665–1676.

In the Examples below, the beneficial effects of curcumin in the severity of pancreatitis as well as the effects of curcumin compounds on NF-κB and AP-1 activation are described. Two experimental models of pancreatitis, cerulein pancreatitis and ethanol/CCK pancreatitis, were used. In the cerulein pancreatitis model, rats received an intravenous infusion of a high dose of a cholecystokinin analogue, cerulein, for 6 hours. In ethanol/CCK pancreatitis model, rats receives an ethanol containing diet for 6 weeks followed by an intravenous infusion of a low dose of cholecystokinin-octapeptide (CCK-8) for 6 hours.

As described in the Examples, curcumin improved the severity of pancreatitis which was assessed by measurements of serum amylase and lipase, pancreatic trypsin and neutrophil infiltration. Curcumin markedly inhibited NF-κB and AP-1 activation as measured by gel-shift assays (EMSAs) and degradation of IκB proteins and the induction of mRNA expression for cytokines IL-6 and TNFα, chemokine KC, and iNOS in pancreas. Curcumin also blocked CCK induced NF-κB and AP-1 activation in isolated pancreatic acini.

In some of the Examples, native curcumin having the following structural formula:

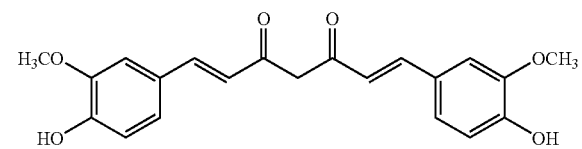

was used. Where indicated, curcumin was administered intravenously. Curcumin is not soluble in water or saline. When dissolved in dimethylsulfoxide (DMSO) and then diluted in saline for the intravenous infusion, curcumin precipitated in the veins of the rat. Therefore, curcumin in DMSO was administered by continuous intravenous infusion at a rate of 35 mg/kg/hr. Thus, during the 6 hour infusion the animal received a total dose of 200 mg (=0.5 mmole per kg body weight). Control animals received infusion of DMSO at the same rate. Infusion of DMSO did not cause any adverse reaction and did not affect any of the measurements in control animals.

Figure 2:
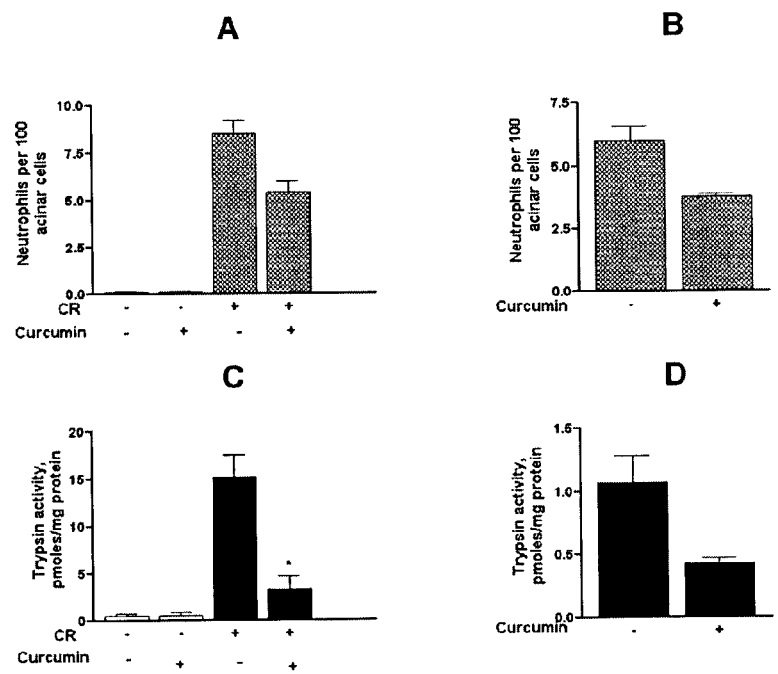
FIG. 2A illustrates neutrophil infiltration from control rats, and rats with cerulein pancreatitis treated without curcumin (CR, −) and rats with cerulein pancreatitis treated with of curcumin (CR, +). Values are means±SE from at least 4 animals for each group. * indicates that the values for animals with pancreatitis receiving curcumin were significantly lower than for those without curcumin (p<0.05).
FIG. 2B shows neutrophil infiltration from rats with ethanol/CCK pancreatitis treated without and with curcumin. Values are means±SE from at least 4 animals for each group. * indicates that the values for animals with pancreatitis receiving curcumin were significantly lower than for those without curcumin (p<0.05).
FIG. 2C shows active trypsin measured using a fluorogenic assay in pancreatic tissue of control rats or rats with cerulein pancreatitis treated without or with curcumin. Values are means+SE from at least 4 rats in each group. * indicates that the values for rats with pancreatitis receiving curcumin were significantly lower than for those without curcumin (p<0.05).
FIG. 2D shows active trypsin measured using a fluorogenic assay in pancreatic tissue of rats with ethanol/CCK pancreatitis treated without or with curcumin. Values are means+SE from at least 4 rats in each group. * indicates that the values for rats with pancreatitis receiving curcumin were significantly lower than for those without curcumin (p<0.05).

FIGS. 1 and 2 demonstrate the effects of intravenous administration of curcumin on measures of pancreatitis in the two experimental models. As illustrated in FIG. 1, curcumin attenuated the increase in serum amylase and lipase (the most commonly used measures of pancreatitis) in both experimental models of pancreatitis. Curcumin inhibited this increase by approximately 50%. As illustrated in FIG. 2, curcumin treatment significantly inhibited the accumulation of neutrophils in the pancreas as well as intrapancreatic trypsin activation in both models of experimental pancreatitis. Intrapancreatic neutrophil accumulation and trypsin activation are two quantitative measures of pancreatitis that were frequently used to measure the amount of inflammation (neutrophils) and the amount of cell injury (trypsin activation). Of note, curcumin's effects were not due to inhibition of the action of CCK or its receptor by measuring the effect of curcumin on pancreatic enzyme secretion in vivo. Additionally, curcumin did not appear to have an effect on CCK-induced secretion.

Figure 3:
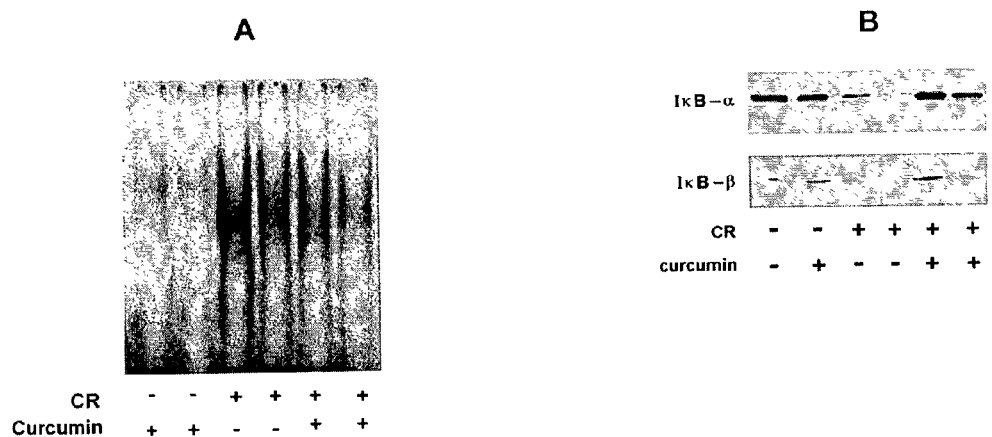
FIG. 3A shows the electromobility shift assays (EMSAs) for NF-κB on nuclear extracts from pancreatic tissue of control rats and rats with cerulein pancreatitis treated with or without curcumin. Each lane represents data for an individual animal representative a group of 4 animals.
FIG. 3B shows the Western blots, using antibody against IκBα and IκBβ, of cytosolic protein extracts from pancreatic tissue of control rats and rats with cerulein pancreatitis treated with or without curcumin. Each lane represents data for an individual animal representative a group of 4 animals.

The experimental results illustrated in FIG. 3 indicate the effects of curcumin on the activation of NF-κB in the pancreas in the high dose cerulein model of pancreatitis. The results in FIG. 3A indicate that the cerulein infusion causes a marked increase in NF-κB activation that is attenuated by the curcumin treatment. NF-κB activation results when inhibitory κBs (IκBs) are released from the inactive NF-κB complex by protein degradation. The results in FIG. 3B demonstrate that cerulein infusion caused decreases in IκBα and IκBβ and that these decreases were prevented by curcumin treatment. The combined results in FIGS. 3A and 3B indicate that in this model of pancreatitis curcumin attenuated the activation of NF-κB by preventing the degradation of the IκBs.

Figure 4:
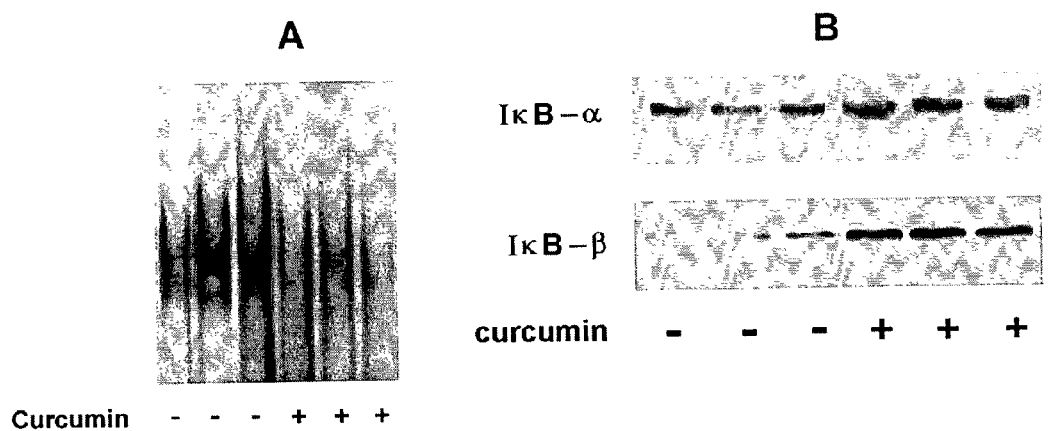
FIG. 4A shows the EMSAs for NF-κB on nuclear extracts from pancreatic tissue of rats with ethanol/CCK pancreatitis treated without or with curcumin.
FIG. 4B shows the Western blots, using antibody against IκBα and IκBβ, of cytosolic protein extracts from pancreatic tissue of rats with ethanol/CCK pancreatitis treated with or without curcumin. Each lane represents data for an individual animal representative a group of 4 animals.

The results in FIG. 4 indicate that curcumin also inhibits NF-κB activation and IκB degradation in the ethanol-sensitization model of pancreatitis.

Figure 5:
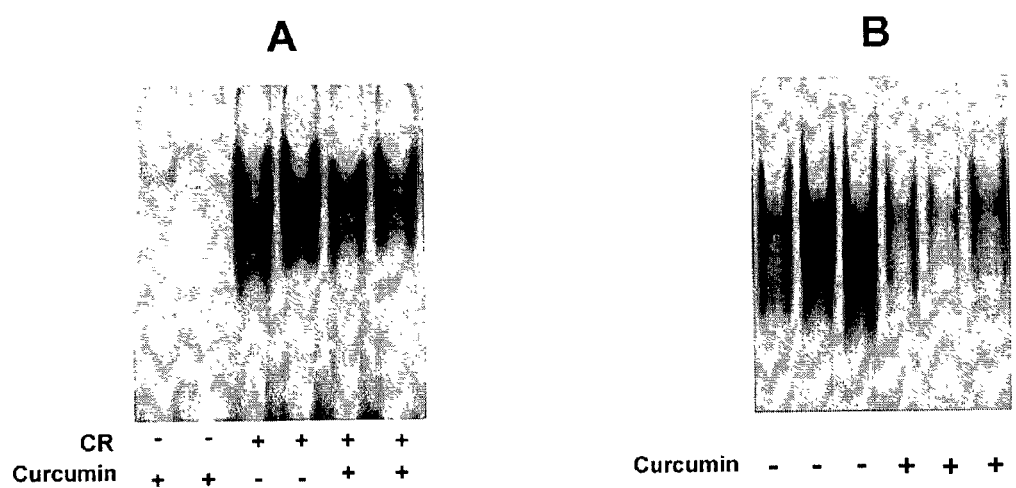
FIG. 5A shows the EMSAs for AP-1 on nuclear extracts from pancreatic tissue of control rats and rats with cerulein pancreatitis treated with or without curcumin.
FIG. 5B shows the EMSAs for AP-1 on nuclear extracts from pancreatic tissue of rats with ethanol/CCK pancreatitis treated without or with curcumin.

As illustrated in FIG. 5, curcumin also inhibited the activation of AP-1 in both models of experimental pancreatitis.

Figure 6:
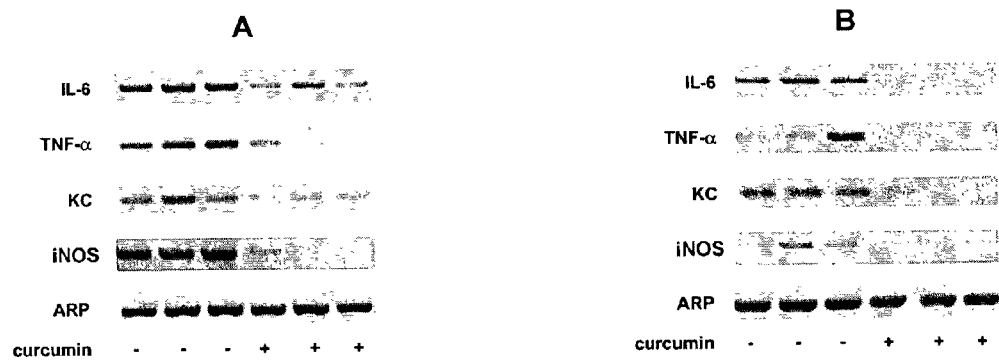
FIG. 6 is a representative RT-PCR for the expression of cytokines and housekeeping gene for the acidic ribosomal phosphoprotein P0 (ARP) in pancreatic tissue of rats with cerulein (A) or ethanol/CCK (B) pancreatitis treated with or without curcumin.

To determine if the effects of curcumin on the activation of the transcription factors resulted in changes in the pancreatic expression of inflammatory molecules, the effects of curcumin on several of these inflammatory molecules were measured. As illustrated in FIG. 6, curcumin attenuated the expression of IL-6, TNFα, KC (the rat analogue of IL-8 and GROα) and iNOS in both experimental models.

Figure 7:
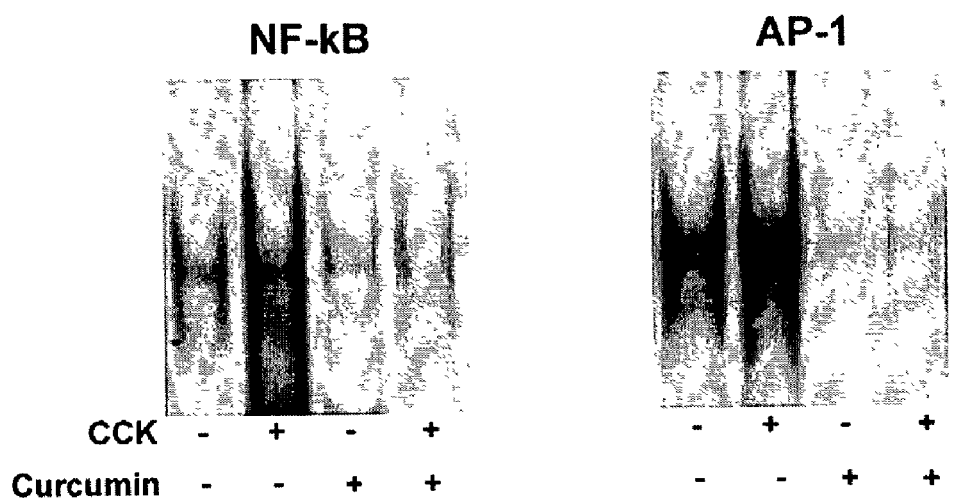
FIG. 7 shows that curcumin inhibits CCK-induced activation of NF-κB and AP-1 in vitro in isolated acinar cells.

To demonstrate that in vitro preparations of pancreatic acini may be used to determine the effect of curcumin compounds on NF-κB and AP-1 activation, the effects of curcumin on CCK-induced activation in this preparation was determined and the results are illustrated in FIG. 7. The results demonstrate the CCK-8 activates both transcription factors and that curcumin attenuates the activation.

Although curcumin exhibits beneficial effects on pancreatitis, curcumin has limited solubility, i.e. insoluble in water or ethanol. Additionally, curcumin is not highly potent in its ability to inhibit NF-κB activation in pancreatic acini. Thus, fluoride derivatives of curcumin were synthesized using SelectFluor according to the manufacturer's instructions. The mixture of substrates and products from the reaction were not purified before testing in the experiment shown in FIG. 8. The whole mixture was tested with the assumption that a product in the mixture with greater potency would be detected in the assay despite the presence of the other products. Additionally, nitro and methoxy derivatives of curcumin that were synthesized and purified by Dr. Yang. (Chul-Hak Yang, Ph.D., from School of Chemistry and Molecular Engineering, College of Natural Science, Seoul National University, Seoul, South Korea) were tested. See Korean Patent Application No. KR 10-2000-0061113, entitled "Novel Synthetic Curcuminoids Which Inhibit Jun-fos Activity", filed on 17, Oct. 2000, which is herein incorporated by reference. The structures of the curcumin compounds obtained from Dr. Yang are listed in Table 1.

TABLE 1

| Name | $R_1$ | $R_2$ | $R_3$ | $R_4$ |
|------|-------|-------|-------|-------|
| CHC001 | $OCH_3$ | H | H | H |
| CHC002 | $OCH_3$ | $OCH_3$ | $OCH_3$ | H |
| CHC003 | $OCH_3$ | H | $OCH_3$ | H |
| CHC004 | $OCH_3$ | $OCH_3$ | H | H |
| CHC005 | H | $OCH_3$ | H | H |
| CHC006 | H | H | H | H |
| CHC007 | $NO_2$ | OH | H | H |
| CHC008 | OH | H | H | H |
| CHC009 | $NO_2$ | H | H | H |
| CHC011 | H | $NO_2$ | H | H |
| BJC004 | $NO_2$ | $CH_3$ | H | H |
| BJC005 | $NO_2$ | OH | $OCH_3$ | H |

All of the curcumin compounds obtained from Dr. Yang, except for CHCO02, and the fluorinated derivatives were soluble in water at concentration up to about 1 to about 2 mM.

The effects of curcumin compounds on activation of NF-κB in pancreatic acini from rat stimulated with cholecystokinin-octapeptide (CCK-OP) were tested. Inhibition of NF-κB activation was observed with all curcumin compounds at 100 μM concentrations (data not shown). In contrast, only the nitro derivative, CHC011, and the fluorinated curcumin compound significantly inhibited NF-κB activation when used at concentrations of 10 μM as shown in FIG. 8.

Figure 8:
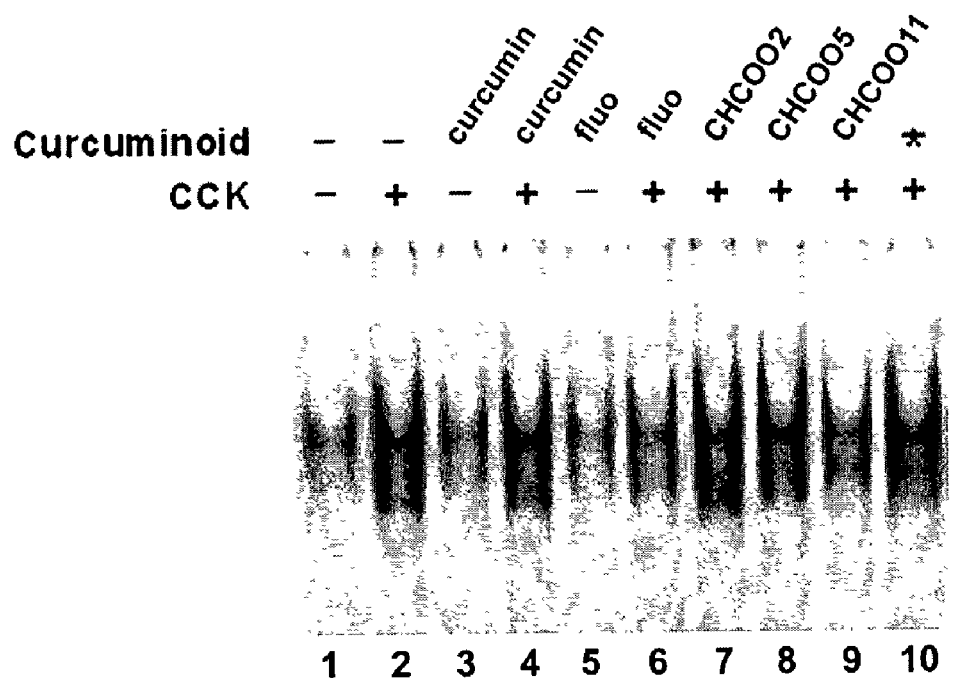
FIG. 8 shows the effects of curcumin derivatives on CCK-induced NF-κB activation in isolated acinar cells. In lane 10 (*), the reaction presented in lane 2 was repeated in the presence of 10 μM CHCO11 in the EMSA assay.

Also as shown in FIG. 8, curcumin compounds did not affect the basal NF-κB binding activity in control cells, i.e. incubated without CCK. Finally, when added directly to the reaction, curcumin compounds did not affect the interaction between NF-κB and its DNA binding site. See FIG. 8 for CHCO11 derivative. These results indicate that the effect of curcumin compounds is caused by their inhibition of NF-κB activation in the acinar cells.

Therefore, curcumin compounds have significant potential for development into agents that can be used for the treatment of pancreatitis. Thus, the present invention is directed to compounds and compositions comprising curcumin compounds for treating, preventing, or inhibiting pancreatitis. The present invention is also directed to methods of treating, preventing, or inhibiting pancreatitis in a subject which comprises administering to the subject an effective amount of at least one curcumin compound.

In addition to its role in inflammation, NF-κB activation is generally known to inhibit apoptosis. See Aggarwal B B (2000); Wulczyn F G, et al. (1996); and Yamamoto Y and Gaynor R B (2001). NF-κB inhibits apoptosis by inhibiting activation of caspases, the key mediators of apoptosis. See Aggarwal B B (2000); Deveraux Q L and Reed J C (1999) Genes Dev 13:239–252; and Wolf B B and Green D R (1999) J Biol Chem 274:20049–20052, which are herein incorporated by reference. The death of parenchymal cells in pancreatitis occurs via both necrosis and apoptosis and the severity of pancreatitis was less in models with increased apoptosis. See Gukovskaya A S, et al. (1996) and Kaiser A M et al. (1995) Am J Physiol 269:C1295–C1304.

To determine a potential effect of curcumin on apoptosis in the experimental models under study, the caspase-3-like (DEVDase) activity in the pancreas was measured. Activation of caspase-3 is a final step in the caspase cascade. See Wolf B B (1999). Caspase-3 mediates CCK-induced apoptosis in isolated pancreatic acinar cells. See Gukovskaya A S, et al. (2002). NF-κB negatively regulates caspase activation in CCK-stimulated acinar cells. See Gukovskaya A S, et al. (1999).

Figure 9:
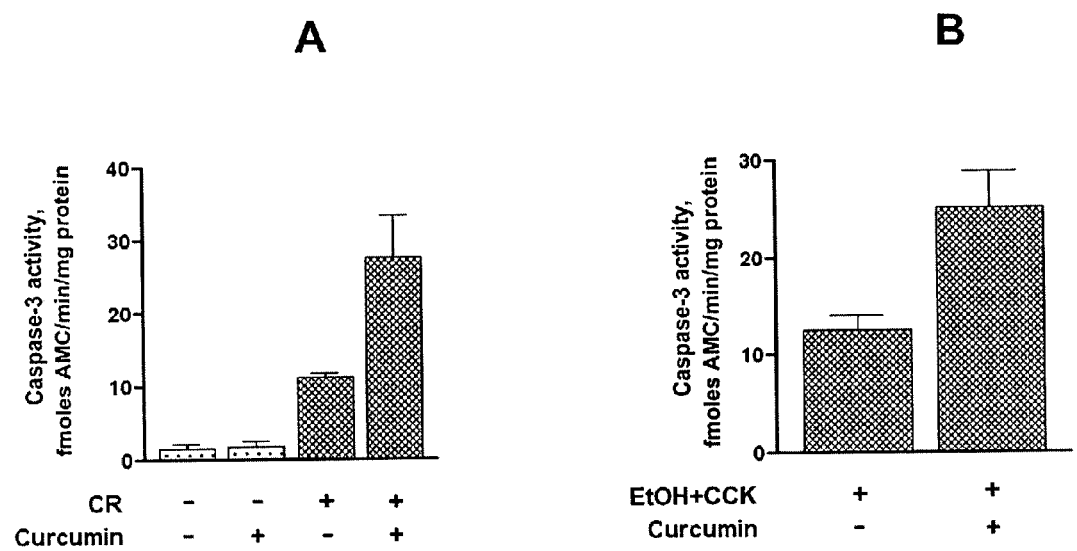
FIG. 9 shows Caspase-3-like (DEVDase) activity in pancreatic tissue lysates from rats with cerulein (CR) pancreatitis (A) and rats with EtOH+CCK pancreatitis (B), both treated without and with curcumin. Values are means * SE from at least 4 animals in each group. * indicates that the values for rats with pancreatitis receiving curcumin were significantly higher than for those without curcumin p<0.05.

As shown in FIG. 9, curcumin augmented, by greater than about 2-fold, the increase in DEVDase activity in both models, thereby suggesting that the activated state of NF-κB attenuates caspase activity (and probably apoptosis) in pancreatitis.

It has been speculated that an increase in apoptosis alleviates the severity of experimental pancreatitis. See Gukovskaya A S, et al. (1996) and Kaiser A M, et al. (1995). That is, the increase in apoptosis results in a concomitant decrease in necrosis. Thus, the effect of agents that inhibit NF-κB activation is to improve pancreatitis not only by decreasing inflammation but by also decreasing necrosis by increasing apoptosis.

Figure 10:
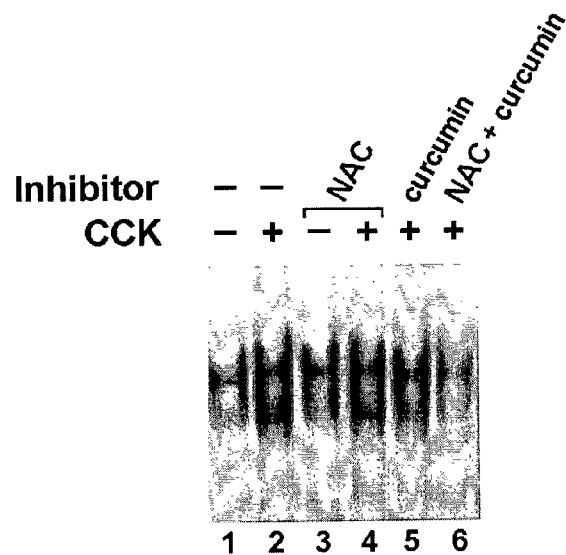
FIG. 10 shows the effects of curcumin and N-acetylcysteine alone and in combination on NF-κB activation in isolated acinar cells.

As indicated earlier, it is possible that the mechanisms by which curcumin compounds and inhibitors of ROS attenuate NF-κB activation differ. In order to determine if there is actually such a difference, the experiment set forth in FIG. 10 was designed to measure the effects of curcumin and N-acetylcysteine alone and in combination on NF-κB activation stimulated by CCK in rat pancreatic acini. N-acetylcysteine is an antioxidant believed to act as both ROS scavenger and glutathione precursor. See Flohe L, et al. (1997) Free Radic Biol Med 22:1115–1126. As shown in FIG. 10, curcumin and N-acetylcysteine when given together have a synergistic effect on inhibiting NF-κB activation in CCK-stimulated pancreatic acinar cells. That is, each agent produced very little inhibition when used alone at low (sub-maximal) concentrations. When both agents were administered, however, the response was pronounced and much greater than would be expected if curcumin and N-acetylcysteine acted through the same mechanism.

These results indicate that there are at least two distinct signaling pathways that mediate NF-κB activation. Therefore, therapies for treating, preventing, or inhibiting pancreatitis may include methods that target one signaling pathway or both. Preferred methods of the present invention include the simultaneous inhibition of both NF-κB activation signaling pathways to provide a synergistic effect to treat, prevent, or inhibit inflammatory diseases that are mediated by NF-κB activation such as pancreatitis.

Therefore, the present invention provides a method of treating, preventing, or inhibiting inflammation related to NF-κB activation, such as pancreatitis which comprises identifying a subject suffering from such inflammation, administering to the subject an effective amount of at least one curcumin compound.

Therefore, as used herein, "curcumin compound" refers to a compound having the following structural formula:

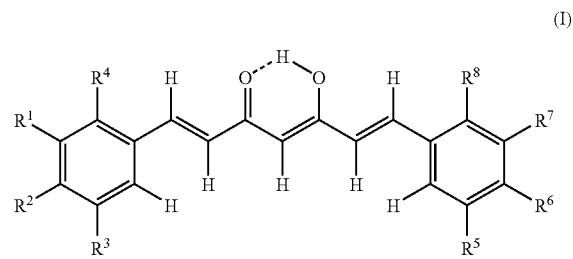

(I)

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl, and salts and esters thereof. In preferred embodiments, $R^1$ to $R^6$ are each independently H, OH, $NO_2$, and $OCH_3$.

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (Bu), isobutyl (i-Bu), t-butyl (t-Bu), ethenyl, pentenyl, butenyl, propenyl, ethynyl, butynyl, propynyl, pentynyl, hexynyl, and the like, which may be unsubstituted (i.e., contain only carbon and hydrogen) or substituted by one or more suitable sustituents as defined below (e.g., one or more halogen, such as F, Cl, Br, or I, with F and Cl being preferred). A "lower alkyl group" is intended to mean an alkyl group having from 1 to 8 carbon atoms in its chain.

A "cycloalkyl" is intended to mean a non-aromatic monovalent monocyclic, bicyclic, or tricyclic radical comprising 3–14 carbon ring atoms, each of which may be saturated or unsaturated, and which may be unsubstituted or substituted by one or more suitable substituents as defined below, and to which may be fused one or more heterocloalkyl groups, aryl groups, or heteroaryl groups, which themselves may be unsubstituted or substituted by one or more substituents. Illustrative examples of cycloalkyl groups include the following moieties:

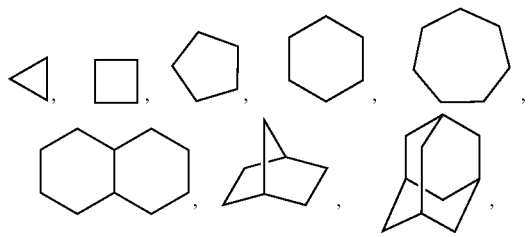

-continued

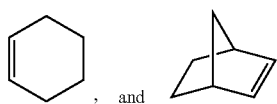

A "heterocycloalkyl" is intended to mean a non-aromatic monovalent monocyclic, bicyclic, or tricyclic radical, which is saturated or unsaturated, comprising 3–18 ring members, which includes 1–5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

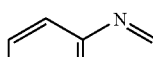

An "aryl" is intended to mean an aromatic monovalent monocyclic, bicyclic, or tricyclic radical comprising 6, 10, 14, or 18 carbon ring members, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

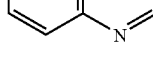

-continued

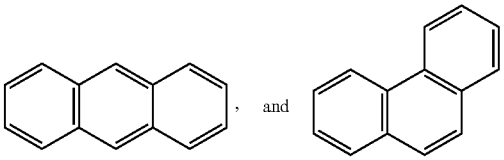

A "heteroaryl" is intended to mean an aromatic monovalent monocyclic, bicyclic, or tricyclic radical comprising 4–18 ring members, including 1–5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

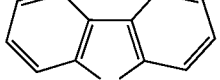

A "heterocycle" is intended to mean a heteroaryl or heterocycloalkyl group (each of which, as defined above, are optionally substituted).

The terms "aryl" (Ar) and "heteroaryl" refer to monocyclic and polycyclic unsaturated or aromatic ring structures, with "aryl" referring to those that are carbocycles and "heteroaryl" referring to those that are heterocycles.

Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like.

An "acyl" is intended to mean a —C(O)—$R^a$ radical, where $R^a$ is a suitable substituent as defined below.

A "thioacyl" is intended to mean a —C(S)—$R^a$ radical, where $R^a$ is a suitable substituent as defined below.

A "sulfonyl" is intended to mean a —SO$_2$$R^a$ radical, where $R^a$ is a suitable substituent as defined below.

A "hydroxyl" is intended to mean the radical —OH.

An "amino" is intended to mean the radical —NH$_2$.

An "alkylamino" is intended to mean the radical —NHR$^a$, where $R^a$ is an alkyl group.

A "dialkylamino" is intended to mean the radical —NR$^a$R$^b$, where $R^a$ and $R^b$ are each independently an alkyl group.

An "alkoxyl" is intended to mean the radical —OR$^a$, where $R^a$ is an alkyl group. Exemplary alkoxyl groups include methoxyl, ethoxyl, propoxyl, and the like.

An "alkoxycarbonyl" is intended to mean the radical —C(O)OR$^a$, where $R^a$ is an alkyl group.

An "alkylsulfonyl" is intended to mean the radical —SO$_2$R$^a$, where $R^a$ is an alkyl group.

An "alkylaminocarbonyl" is intended to mean the radical —C(O)NHR$^a$, where $R^a$ is an alkyl group.

A "dialkylaminocarbonyl" is intended to mean the radical —C(O)NR$^a$R$^b$, where $R^a$ and $R^b$ are each independently an alkyl group.

A "mercapto" is intended to mean the radical —SH.

An "alkylthio" is intended to mean the radical —SR$^a$, where $R^a$ is an alkyl group.

A "carboxyl" is intended to mean the radical —C(O)OH.

A "carbamoyl" is intended to mean the radical —C(O)NH$_2$.

An "aryloxyl" is intended to mean the radical —OR$^c$, where $R^c$ is an aryl group.

A "heteroaryloxyl" is intended to mean the radical —OR$^d$, where $R^d$ is a heteroaryl group.

An "arylthio" is intended to mean the radical —SR$^c$, where $R^c$ is an aryl group.

A "heteroarylthio" is intended to mean the radical —SR$^d$, where $R^d$ is a heteroaryl group.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wutz, Protecting Groups in Organic Synthesis, 2$^{nd}$ edition, John Wiley and Sons, New York, N.Y. (1991).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; CO$_2$CH$_3$; CONH$_2$; OCH$_2$CONH$_2$; NH$_2$; SO$_2$NH$_2$; OCHF$_2$; CF$_3$; OCF$_3$; and the like. Such moieties may also be optionally substituted by a fused-ring structure or bridge, for example OCH$_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the curcumin compounds may exist as single stereoisomers (i.e., essentially free of other stereoisomers), racemates, or mixtures of enantiomers, diastereomers, or both. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, if the compounds of the present invention are made synthetically, they are used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the curcumin compounds, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the curcumin compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to receptor binding. Provision of such multivalent forms of active receptor-binding compounds with optimal spacing between the receptor-binding moieties may enhance receptor binding. See, for example, Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin) or HSA, peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011–2016; Shan, D. et al., *J Pharm. Sci.*, 86(7):765–767; Bagshawe K., (1995) Drug Dev. Res. 34:220–230; Bodor, N., (1984) Advances in Drug Res. 13:224–331; Bundgaard, H., *Design of Prodrugs* (Elsevier Press, 1985); and Larsen, I. K., *Design and Application of Prodrugs*, Drug Design and Development (Krogsgaard-Larsen et al., eds., Harwood Academic Publishers, 1991).

If the curcumin compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the curcumin compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the inventive compounds and salts may exist in different crystal or polymorphic forms, all of which are intended to be within the scope of the present invention and specified structural formulas.

The curcumin compounds, ROS inhibitors, and compositions comprising both in accordance with the present invention are useful in the treatment of diseases and disorders associated with inflammation related to NF-κB activation, such as pancreatitis, arthritis, inflammatory bowel disease, nephritis, pneumonitis, hepatititis, encephalititis, acute and chronic inflammation, and the like.

The curcumin compounds of the present invention may be used in combination with or as a substitution for treatments of the above conditions. For example, the curcumin compounds, ROS inhibitors, and compositions of the invention may be used alone or in combination with glucocorticoids, cyclooxygenase (COX) inhibitors, or analgesics to treat inflammatory disorders such as rheumatoid arthritis.

A curcumin compounds, ROS inhibitors, and compositions of the present invention may be administered in a therapeutically effective amount to a mammal such as a human or cat. A therapeutically effective amount may be readily determined by standard methods known in the art.

An effective amount of a curcumin compound or a ROS inhibitor, or both is an amount that reduces or inhibits NF-κB activation as compared to a control using methods known in the art. The dosages to be administered can be determined by one of ordinary skill in the art depending on the clinical severity of the disease, the age and weight of the subject, the exposure of the subject to conditions that may precipitate the inflammation or other conditions that modulate the activity NF-κB. Preferred effective amounts of curcumin compounds of the invention ranges from about 1 to about 2400 mg/kg body weight, preferably about 10 to about 1000 mg/kg body weight, and more preferably about 10 to about 500 mg/kg body weight. Preferred topical concentrations include about 0.1% to about 10% in a formulated salve.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the curcumin compound can include a single treatment or, preferably, can include a series of treatments.

In a preferred example, a subject is treated with a curcumin compound, a ROS inhibitor, or both in the range of between about 1 to about 2400 mg/kg body weight, at least one time per week for between about 1 to about 24 weeks, and preferably between about 1 to about 10 weeks. It will also be appreciated that the effective dosage of a curcumin compound, a ROS inhibitor, or both used for treatment may increase or decrease over the course of a particular treatment. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the condition to be treated, and the chosen active compound.

It will be appreciated that the actual dosages of the agents used in the compositions of this invention will vary according to the particular complex being used, the particular composition formulated, the mode of administration, and the particular site, host, and disease being treated. Optimal dosages for a given set of conditions may be ascertained by those skilled in the art using conventional dosage-determination tests in view of the experimental data for a given curcumin compound. Administration of prodrugs may be dosed at weight levels that are chemically equivalent to the weight levels of the fully active forms.

The curcumin compounds of the invention can be incorporated into pharmaceutical compositions suitable for administration. Pharmaceutical compositions of this invention comprise a therapeutically effective amount of a curcumin compound, and an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art.

Except insofar as any conventional media or agent is incompatible with the active compound, use thereof in the compositions is contemplated. Supplementary active compounds can also be incorporated into the compositions. Supplementary active compounds include other anti-inflammatory drugs such as corticosteroids, substance P inhibitors such as capsaicin, resiniferatoxin, or capsaicin analogues, capsaicin-sensitive vanilloid receptor inhibitors such as capsazepine, cyclo-oxygenase inhibitors such as acetylsalicylic acid, and other non-steroidal anti-inflammatory agents such as naproxen; polyphenolic compounds such as rutin, catechin, epicatechin, naringin, naringenin, gallotanin, rottlerin and epigallotanin.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, the curcumin compound of the present invention is dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can comprise the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Preferred formulations for oral formulations include microcrystalline tablets, gelatin capsules, or the like.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated comprising a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may comprise formulatory agents such as suspending, stabilizing and/or dispersing agents.

Pharmaceutical compositions suitable for injectable use include sterile aqueous solutions (where water soluble) or dispersions and sterile powders for the extemporaneous preparation of sterile injectable solutions or dispersion. Aqueous injection suspensions may comprise substances which increase the viscosity of the suspension, such as sodium carboxymethyl cellulose, sorbitol, or dextran. Optionally, the suspension may also comprise suitable stabilizers or agents which increase the solubility of the compounds to allow for the preparation of highly concentrated solutions. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes.

For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium comprising, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating a therapeutically effective amount of a compound of the invention in an appropriate solvent with one or a combination of ingredients enumerated above, as required, followed by filtered sterilization. Generally, dispersions are prepared by incorporating the curcumin compound into a sterile vehicle which comprises a basic dispersion medium and the required other ingredients from those enumerated above. In the case of sterile powders for the preparation of sterile injectable solutions, the preferred methods of preparation are vacuum drying and freeze-drying which yields a powder of the active compound plus any additional desired ingredient from a previously sterile-filtered solution thereof.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, foams, powders, sprays, aerosols or creams as generally known in the art.

For example, for topical formulations, pharmaceutically acceptable excipients may comprise solvents, emollients, humectants, preservatives, emulsifiers, and pH agents. Suitable solvents include ethanol, acetone, glycols, polyurethanes, and others known in the art. Suitable emollients include petrolatum, mineral oil, propylene glycol dicaprylate, lower fatty acid esters, lower alkyl ethers of propylene glycol, cetyl alcohol, cetostearyl alcohol, stearyl alcohol, stearic acid, wax, and others known in the art. Suitable humectants include glycerin, sorbitol, and others known in the art. Suitable emulsifiers include glyceryl monostearate, glyceryl monoleate, stearic acid, polyoxyethylene cetyl ether, polyoxyethylene cetostearyl ether, polyoxyethylene stearyl ether, polyethylene glycol stearate, propylene glycol stearate, and others known in the art. Suitable pH agents include hydrochloric acid, phosphoric acid, diethanolamine, triethanolamine, sodium hydroxide, monobasic sodium phosphate, dibasic sodium phosphate, and others known in the art. Suitable preservatives include benzyl alcohol, sodium benzoate, parabens, and others known in the art.

For administration to the eye, the compound of the invention is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., comprising conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) comprises VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied, for example: other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers comprising the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit comprising a predetermined quantity of active compound calculated to produce the desired therapeutic effect in association with the required pharmaceutical carrier.

The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The curcumin compounds of the present invention may be prepared using reaction routes, synthesis schemes and techniques available in the art using starting materials that are readily available.

The following examples are intended to illustrate but not to limit the invention.

EXAMPLE 1

Cerulein-Induced Pancreatitis Model

5 µg/kg/h of Cerulein (American Peptide Co., Sunnyvale, Calif.) or vehicle control was administered to male Sprague-Dawley rats (275–350 g; Harlan, Madison, Wis.) by continuous 6-hour intravenous infusion by conventional methods known in the art. See Gukovskaya A S, et al. (1997) J. Clin. Invest. 100:1853–1862; Gukovsky I, et al. (1998) Am. J. Physiol. 275:G1402–G1414; and Zaninovic V, et al. (2000) Am. J. Physiol. 279:G666–G676, which are herein incorporated by reference. Animals were euthanized by $CO_2$-induced asphyxiation, and blood and the pancreas were harvested for measurements.

Curcumin (Sigma Chemical, St. Louis, Mo.) was dissolved in dimethyl sulfoxide (DMSO) and administered to each animal by i.v. infusion together with cerulein at a dose of 35 mg/kg/h. Thus, during the 6-hour treatment, each animal received a total of 200 mg/kg (0.5 mmol/kg) of curcumin.

Serum amylase and lipase were measured under contract using a Hitachi 707 analyzer (Antech Diagnostics, Irvine Calif.) and methods known in the art. Curcumin significantly inhibited the increases in serum amylase and lipase as provided in FIGS. 1A and 1B, respectively. Thus, curcumin inhibits hyperamylaseimia and hyperlipasemia in pancreatitis.

EXAMPLE 2

Ethanol/CCK-Induced Pancreatitis Model

An ethanol/CCK-induced pancreatitis model as previously described was used. See Pandol S J, et al. (1999). Specifically, Sprague-Dawley rats (400–500 g; Harlan, Madison, Wis.) were given an intragastric infusion of ethanol-containing or control diet for 6 weeks followed by 6-hour infusion of a low dose (3000 pmol/kg/h) CCK-8 (Peninsula Laboratories, Belmont, Calif.). The low dose of CCK-8 does not cause pancreatitis by itself; it only causes pancreatitis in animals that receive to ethanol-containing diet for 6 weeks. CCK-8 causes pancreatitis in both rats and mice by stimulating the activation of the inflammatory signals, i.e. NF-κB and AP-1, in the pancreatic acinar cell. Animals were euthanized by $CO_2$-induced asphyxiation, and blood and the pancreas were harvested for measurements.

Curcumin (Sigma Chemical, St. Louis, Mo.) was dissolved in dimethyl sulfoxide (DMSO) and administered to each animal by i.v. infusion together with CCK-8 at a dose of 35 mg/kg/h. Thus, during the 6-hour treatment, each animal received a total of 200 mg/kg (c. 0.5 mmol/kg) of curcumin.

Serum amylase and lipase were measured under contract using a Hitachi 707 analyzer (Antech Diagnostics, Irvine Calif.) and methods known in the art. As provided in FIG. 1C, curcumin significantly inhibited the increases in serum amylase and lipase. Thus, curcumin inhibits hyperamylaseimia and hyperlipasemia in pancreatitis.

EXAMPLE 3

Histological Evaluation

Pancreatic tissue from control samples and test samples from Examples 1 and 2 were fixed in 10% buffered formaldehyde, then embedded in paraffin, sectioned, stained with hematoxylin and eosin (H&E), and examined by light microscopy. See Gukovskaya A S (1997) J Clin Invest 100:1853–1862; Gukovskaya A S, et al. (1996) Gastroenterology 110:875–884; Gukovskaya A S, et al. (2002) Gastroenterology 122:974–984; and Pandol S J, et al. (1999) which are herein incorporated by reference.

Histological evaluation of the tissue samples showed that treatment with curcumin compounds improved pancreatic histology (data not shown).

EXAMPLE 4

Neutrophil Inflitration Assay

Neutrophil infiltration of pancreatic tissue was examined using methods known in the art. See Gukovskaya A S, et al. (1997); Gukovskaya A S, et al. (2002); Pandol S J, et al. (1999); Sandoval D, et al. (1996); and Vaquero E, et al. (2001). The pancreas was cut into about 2 to about 3 mm pieces and fixed in 4% paraformaldehyde for 2 hours. The tissue was then frozen in liquid nitrogen. 8-μm-thick serial cryostat sections of pancreatic tissue from control samples and test samples from Examples 1 and 2 were cut and mounted on glass slides. The slides were placed in phosphate buffered saline (PBS) for 5 minutes. This was repeated twice. Then the slides were transferred into blocking buffer (PBS containing 5% (wt/vol) goat serum, 0.5% bovine serum albumin (wt/vol) and 0.1% gelatin(wt/vol) for 1 hour at room temperature.

Then the slides incubated with FITC-conjugated rabbit anti-rat neutrophil antibody (Accurate, Westbury, N.Y.) (diluted 1:120 in the blocking buffer) for 3 hours at room temperature. The slides were the transferred into the blocking buffer, incubated for 5 minutes, and repeated 4 times. Finally, coverslips were mounted over the tissue samples on the slide with the addition of anti-fading medium. The number of infiltrating neutrophils was obtained by counting the neutrophils at 40× magnification in an average of 50 fields covering at least about 1,000 acinar cells. For each sample, neutrophil numbers were expressed as a percentage of acinar cells.

As shown in FIGS. 2A and 2B, treatment with curcumin compounds inhibited neutrophil infiltration in the pancreas by greater than about 50%. FIG. 2A illustrates neutrophil infiltration from control rats, rats with cerulein pancreatitis treated without curcumin (CR,−) and rats with cerulein pancreatitis treated with curcumin (CR,+). FIG. 2B shows neutrophil infiltration from rats with ethanol/CCK pancreatitis treated without and with curcumin. Therefore, curcumin compounds may be used to prevent neutrophil infiltration in the pancreas.

EXAMPLE 5

Trypsin Activation Assay

Pancreatic tissue homogenates were prepared by methods known in the art. See Gukovskaya A S, et al. (2002); Gukovsky I, et al. (1998); Sandoval D, et al. (1996) Gastroenterology 111:1081–1091; and Vaquero E, et al. (2001), which are herein incorporated by reference. Active trypsin was measured in the pancreatic tissue homogenates by using a specific substrate, Boc-GLn-Ala-Arg-A MC (Bachem, Torrance, Calif.). See Kawabata S. et al. (1988) Eur. J. Biochem. 172:17–25, which is herein incorporated by reference. Cleavage of the substrate by trypsin releases 7-amino-4-methylcoumarin (AMC), which emits fluorescence at 440 nm with excitation at 380 nm. Trypsin activity in each sample was determined using a standard curve for purified trypsin.

Specifically, about ⅓ of rat pancreas was homogenized in 2 ml ice-cold buffer A (5 mM MES, pH 6.5; 1 mM MgSO4, 250 mM sucrose). Then 2 ml of buffer B (50 mM Tris, pH 8.0; 150 mM NaCl, 1 mM $CaCl_2$, 0.1 mg/ml BSA) was mixed with 25 μl of the homogenate and kept on ice. Then 2 μl of 20 mM substrate solution (20 mM Boc-Gln-Ala-Arg-AMC.HCl in DMSO) was added to start the reaction. The sample was mixed well and incubated at 37° C. The reaction product was measured with a spectrofluorimeter for 20 minutes at ex=380 nm; em=440 nm.

FIGS. 2C and 2D show active trypsin amounts as measured with a fluorogenic assay in pancreatic tissue of control rats and rats with cerulein (CR) pancreatitis (2C) and rats with EtOH+CCK pancreatitis (2D), both treated with and without curcumin. In the EtOH+CCK model, the basal level of active pancreatic trypsin in ethanol-fed rats was 0.1 pmol/mg protein (n=3), and was unaffected by curcumin. However, as shown in FIG. 2C, curcumin treatment inhibited the intrapancreatic trypsin activation in the cerulein model by greater than about 70%. As shown in FIG. 2D, curcumin treatment inhibited the intrapancreatic trypsin activation in the EtOH+CCK model by greater than about 50%.

EXAMPLE 6

Pancreatic Activation of NF-κB and IκB Degradation and AP-1 Assays

To determine whether curcumin compounds inhibit pancreatic activation of NF-κB, electromobility shift assays (EMSAs) for NF-κB on nuclear extracts from pancreatic tissue EMSA was performed using methods known in the art. See Blinman T A, et al. (2000); Gukovskaya A S, et al.

(1997); Gukovsky I, et al. (1998); Pandol S J, et al. (1999); Vaquero E, et al. (2001); and Zaninovic V, et al. (2000).

Specifically, aliquots of nuclear extracts with equal amounts of protein (about 2 to about 10 mg) were mixed in 20 µl reactions with a buffer containing 10 mM HEPES (pH 7.8), 50 mM KCl, 0.1 mM EDTA, 1 mM DTT, 10% (vol/vol) glycerol, and 3 µg of poly(dI-dC). Binding reactions were started by the addition of c. 60,000 cpm of $^{32}$P-labeled DNA probe and allowed to proceed for about 20 to about 25 minutes at room temperature. The oligonucleotide probe for NF-κB:

5'-GCAGAGGGGACTTTCCGAGA (SEQ ID NO: 1), containing a consensus κB binding site (underlined); or the AP-1 oligo probe:

5'-GGCTTGATGAGTCAGCCGGAA (SEQ ID NO: 2), containing phorbol ester responsive element (TRE, underlined), were annealed with their complementary strands and end-labeled using Klenow DNA polymerase I (Stratagene, La Jolla, Calif.).

The samples were electrophoresed at room temperature in 0.5×TBE buffer (1× TBE: 89 mM Tris base, 89 mM boric acid, 2 mM EDTA) on a non-denaturing 4.5% polyacrylamide gel at 200 V. The gels were dried and directly analyzed in the PhosphorImager (Molecular Dynamics, Sunnyvale, Calif.).

FIG. 3A shows the electromobility shift assays (EMSAs) for NF-κB on nuclear extracts from pancreatic tissue of control rats and rats with cerulein pancreatitis treated with or without curcumin. Each lane represents data for an individual animal representative a group of 4 animals. Virtually no NF-κB activity was detected in control (vehicle-infused) rats treated either without or with curcumin. FIG. 4A shows the EMSAs for NF-κB on nuclear extracts from pancreatic tissue of rats with ethanol/CCK pancreatitis treated without or with curcumin. The results in FIGS. 3A and 4A indicate that curcumin inhibits NF-κB activation in the pancreas in both models of pancreatitis.

Since NF-κB activation results when the inhibitory-κB proteins (IκB's) are released from the NF-κB complex by degradation in the proteasome and cerulein hyperstimulation causes IκB degradation in the pancreas, IκB degradation was analyzed. IκBα and IκBβ levels were measured in cytosolic protein extracts from pancreatic tissue, prepared according to Example 12, by Western blot analysis using polyclonal antibodies sc-371 and sc-945, respectively (Santa Cruz Biotechnology, Santa Cruz, Calif.) using methods known in the art. See Gukovsky I, et al. (1998).

Specifically, IκBα and IκBβ levels were measured in cytosolic protein extracts from pancreatic tissue by Western blot analysis using polyclonal antibodies sc-371 and sc-945, respectively (Santa Cruz Biotechnology, Santa Cruz, Calif.). See Gukovsky I, et al. (1998). Specifically, proteins in the cytosolic extract were separated by SDS-PAGE at 120 V using precast Tris-glycine gels and Mini-Cell gel apparatus (Novex, San Diego, Calif.). Separated proteins were electrophoretically transferred to polyvinylidene difluoride membrane for 2 hours at 30 V, using a Novex blot module. Nonspecific binding was blocked by overnight incubation of the membrane in 5% (wt/vol) nonfat dry milk in Tris-buffered saline (TBS, pH 7.5). Blots were then incubated for 2 hours at room temperature with primary antibodies in antibody buffer containing 1% (wt/vol) nonfat dry milk in TTBS (0.05% vol/vol Tween 20 in TBS), washed three times with TTBS, and finally incubated for 1 hour with a peroxidase-labeled secondary antibody in the antibody buffer. Blots were developed for visualization using enhanced chemiluminescence detection kit (Pierce Chemical, Rockford, Ill.).

As shown in FIG. 3B, curcumin prevented IκB degradation in cerulein pancreatitis while it did not change IκBα and IκBβ levels in control animals. Likewise, FIG. 4B shows that curcumin treatment prevented IκB degradation in EtOH+CCK pancreatitis.

The combined results provided in FIGS. 3 and 4 indicate that in both pancreatitis models, curcumin attenuated pancreatic activation of NF-κB by preventing the degradation of IκB's.

EXAMPLE 7

CCK-Induced NF-κB and AP-1 Activation Assay

To confirm that the effects of curcumin occur in the pancreatic acinar cell, the effects of curcumin on the activation of NF-κB and AP-1 in vitro in CCK-stimulated pancreatic acini. Pancreatic acini were prepared from rat pancreas using the collagenase digestion method as described by Pandol S J, et al. (1982) J. Biol. Chem. 257:12024–12029, which is herein incorporated by reference, and then incubated at 37° C. in 199 medium (GIBCO, Rockville, Md.) known in the art. See Blinman T A, et al. (2000); Gukovskaya A S, et al. (1997); Gulkovsky I, et al. (1998); and Zaninovic V, et al. (2000).

Rat pancreatic acinar cells were incubated for 1 hour with and without 10 µM or 100 µM of the test curcumin compound (curcumin, fluorinated curcumin (fluo), CHCOO2, CHCOO5 or CHO11), followed by incubation with 0.1 µM CCK or vehicle for 30 minutes.

FIGS. 5A and 5B show that AP-1 is activated in the pancreas in both models of pancreatitis. Thus, treatment with curcumin markedly attenuated AP-1 activation in the cerulein pancreatitis model and almost completely blocked it in the ethanol/CCK pancreatitis model.

EXAMPLE 8

Pancreatic Secretion Assays

To rule out the possibility that the effect of curcumin was through inhibition of the action of cerulein or CCK-8 on CCK receptor activation, the effect of pancreatic secretion was tested.

A. In vivo Pancreatic Secretion Assay

Pancreatic secretion in test rats was measured in vivo by methods known in the art. See Gukovskaya A S, et al. (2002). Briefly, biliopancreatic secretion was allowed to drain freely for 30 minutes before initiation of the experiment. Then secretion was collected in tubes in 10-minute fractions to determine the basal amylase output, after which 0.25 µg/kg cerulein was given as an i.v. bolus and collection continued for 40 minutes in a similar manner. Collection volumes were measured by weigh, and the amylase output was calculated by determining amylase concentration in the collected fractions. The mean amylase output obtained from two consecutive 10-minute fractions after the stabilization period was taken as the basal secretion and considered as 100%. The results were expressed as percentage increase over basal amylase output 40 minutes after cerulein or vehicle infusion.

The cerulein-induced amylase secretion in rats that did not receive curcumin was 980±30% (n=3) of the basal amylase output (prior to administration of cerulein). In rats treated with curcumin, the cerulein-induced amylase secretion was 1000±37% (n=4) of the basal, the two values were deemed to be not statistically different. These data indicate that curcumin administration did not impair cerulein (or CCK) interaction with its receptor on acinar cells as well as the immediate signaling, i.e. G-protein coupling, from the receptor.

B. Secretion in Isolated Acinar Cells

The effect of curcumin on amylase secretion in isolated acinar cells was assayed. Specifically, acinar cells were isolated using a collagenase digestion technique known in the art. Animals were sacrificed with $CO_2$. The pancreas was removed and trimmed from mesentary and fat. Then the pancreas was injected with about 3 ml of digesting medium comprising 1.0 mg collagenase (Worthington, CLSPA, 10,000 U per 2.6 ml $H_2O$) in 15 ml of 0.2% BSA solution (300 ml MJJ (13.92 g NaCl, 1.07 g KCl, 0.69 g $NaH_2PO_4$, 1.31 g pyruvate, 1.65 g fumarate, 2.02 g glutamate, 5.0 g glucose, 0.2 g trypsin inhibitor, 50 ml 50× Minimal Eagle Aminoacids per 2L), 60 ml HEPES (150 mM), 3.6 ml 5% glutamine, 3.6 ml Vitamins Eagle (100×), 7.2 ml $CaCl_2$ (100 mM), 3.6 ml $MgCl_2$ (100 mM), 0.72 g BSA (Sigma, Fraction V) pH 7.4) and incubated for 3 consecutive 15 minute periods at 37° C. in 25 ml flask with vigorous shaking (e.g., Dubnoff incubator at 160 oscillation/min).

After each period, the digestion solution was removed, replaced with 5.0 ml of fresh digesting medium, and oxygenated. Then the samples were vigorously shaken and the digested tissue was passed through a small bore glass pipette. After that, the collagenase was washed off by layering the dispersed acini are layered over 4 ml of 4% BSA (3.8 g BSA per 100 ml of 0.2% BSA solution) in 15 ml centrifuge tube, centrifuging for 5 seconds at 800 rpm (in a benchtop centrifuge). The supernatant was aspirated off, and the pellet washed and centrifuged in 4 ml of 4% BSA plus 4 ml of 0.2% BSA, and the chunks of undigested tissue was removed. The remaining fine cells were spun again in 4% BSA, the pellet was washed and resuspended in incubation medium, pH 7.4.

Amylase secretion was measured. Measurements were done in triplicates. Specifically, pancreatic acinar cells were isolated from 1 rat and resuspended in 40 ml 199 medium supplemented with 0.5% BSA. The samples were divided into seven 5 ml amounts and incubated for 30 minutes without or with CCK at concentrations: $1×10^{-12}$, $1×10^{-11}$, $1×10^{-10}$, $1×10^{-9}$, $1×10^{-8}$, and $1×10^{-7}$ M. At the end of the 30 minute incubation 500 µl aliquots from each sample were placed in centrifuge tubes and the acini were separated from the media by centrifugation. Amylase measurements were performed on these samples after the addition of 500 µl of lysis buffer (150 mM NaCl, 50 mM Tris, pH 7.2, 1% TritonX-100, 1 mM PMSF, 5 µg/ml protease inhibitor cocktail). In a similar way amylase measures were performed on the acinar cells at the beginning of the incubation to determine the content of amylase in the cells before the incubation. Amylase activity was measured in each supernatant sample as well as the cellular sample and values for amylase release were calculated as the percentage of amylase activity in the cells at the beginning of the experiment that was release into the media during the experiment.

The absorbance was read with a spectrophotometer at 405 nm at 37° C. and the amylase activity in the samples was calculated by subtracting initial from the final readings. The results were plotted for each CCK concentration as ratio of amylase in extracellular medium (B) to total amylase content (A): (OD)B/(OD)A.

Amylase release elicited by both maximal (1 nM) and supramaximal (100 nM) doses of CCK-8 was the same in the absence and presence of 100 µM curcumin. In particular, 1 nM CCK-8 increased amylase secretion 6±1 fold (n=3) over basal. Finally, we measured that 100 µM curcumin did not cause additional LDH release in either control acinar cells or cells stimulated with 100 nM CCK-8, indicating that under conditions used, curcumin was not toxic for pancreatic acinar cells.

Therefore, both in vivo and in vitro, curcumin administration did not impair cerulein (or CCK) interaction with its receptor on acinar cells as well as the immediate signaling (i.e., G-protein coupling) from the receptor.

EXAMPLE 9

Assay for Expression of Inflammatory Molecules

To determine whether the effects of curcumin on NF-κB and AP-1 activation translated into changes in the expression of inflammatory molecules, the effect of curcumin on pancreatic mRNA expression of several cytokines and other inflammatory molecules were measured by methods known in the art. See Blinman T A, et al. (2000); Gukovskaya A S, et al. (1999); Gukovsky I, et al. (1998); Pandol S J, et al. (1999); Vaquero E, et al. (2001); and Zaninovic V, et al. (2000).

Briefly, total RNA was obtained from pancreatic tissue with TRI reagent (Molecular Research Center, Cincinnati, Ohio) and its quality was verified by ethidium bromide staining of rRNA bands on a denaturing agarose gel. RNA was reverse-transcribed with the SuperScript II preamplification kit (GIBCO-BRL, Rockville, Md.) and subjected to PCR with the rat gene specific, intron-spanning primers set forth in

TABLE 1

| mRNA | Forward primer | Reverse Primer | Expected Product Size | Genbank Access. No. |
|---|---|---|---|---|
| IL-6 | 5' CAAGAGACTTCCAGCCAGTTG (SEQ ID NO:3) | 5' GCCGAGTAGACCTCATAGTGAC (SEQ ID NO:4) | 612 | M26744 |
| iNOS | 5' TGTGTTCCACCAGGAGATGTTG (SEQ ID NO:5) | 5' CAGTTTCTGGTCGATGTCATGAG (SEQ ID NO:6) | 514 | U03699 |
| TNF-α | 5' TGAACTTCGGGGTGATCGGTC (SEQ ID NO:7) | 5' AGCCTTGTCCCTTGAAGAGAAC (SEQ ID NO:8) | 295 | X66539 |
| MCP-1 | 5' CACTATGCAGGTCTCTGTCACG (SEQ ID NO:9) | 5' GATCTCACTTGGTTCTGGTCCA (SEQ ID NO:10) | 294 | M57441 |
| MIP-2 | 5' CAGTGAGCTGCGCTGTCCAAT (SEQ ID NO:11) | 5' CAGTTAGCCTTGCCTTTGTTCAG (SEQ ID NO:12) | 210 | X65647 |
| ARP | 5' GTTGAACATCTCCCCCTTCTC (SEQ ID NO:13) | 5' ATGTCCTCATCGGATTCCTCC (SEQ ID NO:14) | 402 | Z29530 |
| KC | 5' CAATGAGCTGCGCTGTCAGTG (SEQ ID NO:15) | 5' CTTGGGGACACCCTTTAGCATC (SEQ ID NO:16) | 205 | M86536 |

TABLE 1-continued

| mRNA | Forward primer | Reverse Primer | Expected Product Size | Genbank Access. No. |
|---|---|---|---|---|
| ICAM-1 | 5' GGGTTGGAGACTAACTGGATGA (SEQ ID NO:17) | 5' GGATCGAGCTCCACTCGCTC (SEQ ID NO:18) | 182 | D00913 |

Target sequences were amplified at 56° C. using the same amount of cDNA for all primer sets. The RT-PCR products were all of expected size, and their identity was confirmed by direct sequencing. Negative controls were performed by omitting the RT step or cDNA template from the PCR amplification. The cycle number was adjusted between 22 (for the housekeeping ARP gene) and 36 cycles (for iNOS) in order to yield visible products within the linear amplification range. Resulting RT-PCR products were run on agarose gel and visualized by staining with ethidium bromide.

As shown in FIG. 6, curcumin markedly inhibited pancreatic expression of IL-6, TNF-α, the chemokine KC (rodent analogue of IL-8/GROα), and iNOS in both pancreatic models.

EXAMPLE 10

Activation of NF-κB in Isolated Acinar Cells

To confirm that the effects of curcumin occur in the pancreatic acinar cell, the effects of curcumin on the activation of NF-κB and AP-1 in vitro in CCK-stimulated pancreatic acini was tested.

Rat pancreatic acinar cells were incubated with or without 10 µM or 100 µM of a curcumin compound (curcumin, fluorinated curcumin (fluo), CHCOO2, CHCOO5, or CHO11) for 1 hour, followed by incubation with 0.1 µM CCK or vehicle for 30 minutes. EMSAs for NF-κB and AP-1 were performed on nuclear proteins extracted from each sample as provided above.

FIG. 7 shows that curcumin inhibits CCK-induced activation of NF-κB and AP-1 in vitro in isolated acinar cells. In lane 10 (*), the reaction presented in lane 2 was repeated in the presence of 10 µM CHCO11 in the EMSA assay.

Both NF-κB and AP-1 were activated by 0.1 µM CCK-8 in the acinar cells, which was abolished by curcumin as shown in FIG. 8. Of note, curcumin inhibited not only the CCK-induced activation of these transcription factors but also their basal binding activity on isolated acinar cells, which was more pronounced for AP-1. In lane 10 (*), the reaction presented in lane 2 was repeated in the presence of 10 µM CHCO11 in the EMSA assay.

EXAMPLE 11

Measurement of Capsase-3 Activation

In addition to its role in inflammation, NF-κB activation is generally known to inhibit apoptosis. See Aggarwal B B (2000) and Yamamoto Y and Gaynor R M (2001). NF-κB inhibits apoptosis by inhibiting activation of caspases, which are the main mediators of apoptosis. The death of parenchymal cells in pancreatitis occurs via both necrosis and apoptosis, and the severity of pancreatitis is less in models with increased apoptosis. Activation of caspase-3 is a final step in the caspase cascade. Caspase-3 mediates CCK-induced apoptosis in isolated pancreatic acinar cells. NF-κB negatively regulates caspase activation in CCK-stimulated acinar cells. Thus, to determine a potential effect of curcumin on apoptosis in pancreatitis, capsase-3-like (DEVDase) activity in the pancreas was measured.

Capsase activity was measured by methods known in the art. See Gukovskaya A S, et al. (2002). Briefly, samples of pancreatic tissue were rinsed with ice-cold PBS and homogenized in a lysis buffer comprising 150 mM NaCl, 50 mM Tris-HCL (pH 7.5), 0.5% Igepal CA-630 (Sigma, St. Louis, Mo.), and 0.5 mM EDTA. Lysates were centrifuged for 10 minutes at 16,000× g and the supernatants were collected. Caspase activity was determined at 37° C. in a buffer comprising 25 mM HEPES (pH 7.5), 10% sucrose, 0.1% CHAPS, 10 mM DTT and 20 pM Ac-DEVD-AMC, a specific fluorogenic substrate for measurement of caspase-3-like activity (AnaSpec, San Jose, Calif.). Cleavage of the substrate releases AMC that emits a fluorescent signal with excitation at 380 nm and emission at 440 nm. Fluorescence was calibrated using a standard curve for AMC. The data were expressed as mol AMC/min/mg protein.

Rat pancreatic acinar cells were incubated with or without 100 µM curcumin for 1 hour, followed by incubation with 0.1 µM CCK or vehicle for 30 minutes. As shown in FIG. 9, curcumin augmented, by greater than about 2-fold, the increase in DEVDase activity in both pancreatitis models, thereby suggesting that the activated state of NF-κB in pancreatitis attenuates caspase activity and apoptosis.

EXAMPLE 12

Preparation of Nuclear and Cytosolic Extracts

Nuclear protein extracts were prepared by methods known in the art. See Blinman T A, et al. (2000); Gukovskaya A S, et al. (1997); Gukovsky I, et al. (1998); Pandol S J, et al. (1999); Vaquero E, et al. (2001); and Zaninovic V, et al. (2000). Briefly, samples of pancreatic tissue or isolated acini were rinsed in ice-cold PBS and homogenized in hypotonic Buffer A (20 mM β-glycerophosphate, 10 mM HEPES, pH 7.6, 1.5 mM $MgCl_2$, 10 mM KCl, 10 mM $Na_2MoO4$, 0.1 mM $Na_3VO_4$, 1 mM dithiothreitol (DTT), 1 mM phenylmethylsulfonyl fluoride (PMSF), 5 µg/ml each of protease inhibitors pepstatin, leupeptin, chymostatin, antipain and aprotinin). After incubating on ice for about 20 to about 25 minutes, the nonionic detergent Igepal CA-630 (Sigma, St. Louis, Mo.) was added to a final concentration of 0.3 to 0.4% (v/v), followed by an additional incubation on ice for about 1 to about 2 minutes. The crude nuclear pellet was collected by microcentrifugation for 30 seconds. The supernatant (cytosolic protein) was removed, and the nuclear pellet was resuspended in the high-salt buffer C (25% glycerol, 20 mM β-glycerophosphate, 10 mM HEPES, 1.5 mM $MgCl_2$, 420 mM NaCl, 0.2 mM EDTA, 10 mM $Na_2MoO_4$, 0.1 mM $Na_3VO_4$, 1 mM DTT, 1 mM PMSF, 5 µg/ml each of protease inhibitors pepstatin, leupeptin, chymostatin, antipain and aprotinin. After rotating at 4° C. for up to 1 hour, nuclear membranes were pelleted by microcentrifugation for 10 minutes, and the clear supernatant (nuclear extract) was aliquoted and stored at −80° C. Protein concentration in the nuclear extract was determined by the Bio-Rad protein assay (Bio-Rad Laboratories, Hercules, Calif.).

EXAMPLE 13

Curcumin Compound and ROS Inhibitor Combination

To measure the effects of curcumin compounds and ROS inhibitors, EMSAs and nuclear protein extractions were conducted as provided above.

Rat pancreatic acinar cells were incubated for 1 hour with curcumin (50 µM) and/or N-acetylcysteine (10 µM) followed by incubation with 0.1 µM CCK or vehicle for an additional 30 minutes. EMSAs for NF-κB activation were performed on nuclear proteins extracted from each sample.

As shown in FIG. 10, the combination of curcumin and N-acetylcysteine provided a synergistic effect. Thus, at least one curcumin compound and at least one ROS inhibitor may be used to treat, prevent, inhibit, or modulate pancreatitis in a synergistic manner.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating, modulating, attenuating, or inhibiting pancreatitis which comprises administering to a subject diagnosed with pancreatitis a curcumin compound having the following structural formula

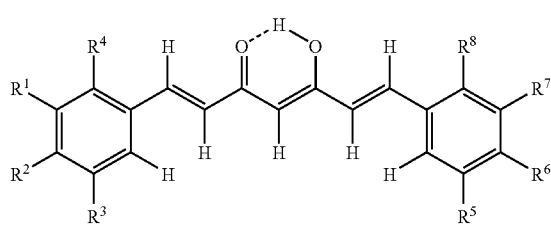

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

2. The method of claim 1, which further comprises administering to the subject at least one reactive oxygen species (ROS) inhibitor selected from the group consisting of N-acetylcysteine, vitamins C, A and E, beta-carotene, allopurinol, carvediol, and coenzyme Q.

3. The method of claim 1, which further comprising administering to the subject at least one supplementary active compound selected from the group consisting of corticosteroids, glucocorticoids, cyclooxygenase (COX) inhibitors, analgesics, substance P inhibitors, vanilloid receptor inhibitors, and other non-steroidal anti-inflammatory agents.

4. A method of modulating or attenuating the expression of IL-6, TNFα, KC, IL-8, or iNOS in pancreatic tissue in a subject diagnosed with pancreatitis comprising administering to said subject a curcumin compound having the following structural formula

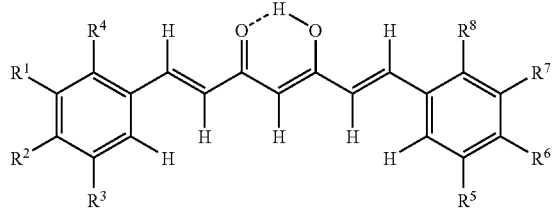

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

5. The method of claim 4, which further comprises administering to the tissue at least one reactive oxygen species (ROS) inhibitor selected from the group consisting of N-acetylcysteine, vitamins C, A and E, beta-carotene, allopurinol, carvediol, and coenzyme Q.

6. The method of claim 4, which further comprises administering to the tissue at least one supplementary compound selected from the group consisting of corticosteroids, glucocorticoids, cyclooxygenase (COX) inhibitors, analgesics, substance P inhibitors, vanilloid receptor inhibitors, and other non-steroidal anti-inflammatory agents.

7. A method of preventing or inhibiting the amount of IκBα and IκBβ from decreasing in pancreatic tissue in a subject diagnosed with pancreatitis comprising administering to said subject a curcumin compound having the following structural formula

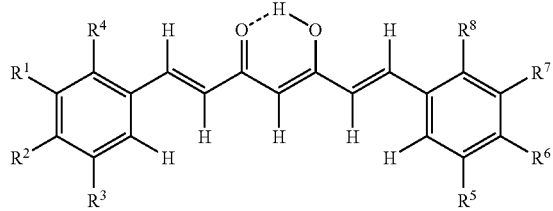

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

8. The method of claim 7, which further comprises administering to the tissue at least one reactive oxygen species (ROS) inhibitor selected from the group consisting of N-acetylcysteine, vitamins C, A and E, beta-carotene, allopurinol, carvediol, and coenzyme Q.

9. The method of claim 7, which further comprises administering to the tissue at least one supplementary compound selected from the group consisting of corticosteroids, glucocorticoids, cyclooxygenase (COX) inhibitors, analgesics, substance P inhibitors, vanilloid receptor inhibitors, and other non-steroidal anti-inflammatory agents.

10. A method of preventing or inhibiting the degradation of IκBα and IκBβ in pancreatic tissue in a subject diagnosed with pancreatitis comprising administering to said subject a curcumin compound having the following structural formula

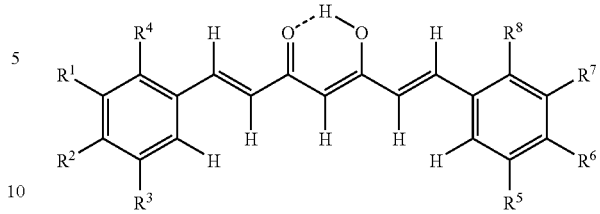

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

11. The method of claim 10, which further comprises administering to the subject at least one reactive oxygen species (ROS) inhibitor selected from the group consisting of N-acetylcysteine, vitamins C, A and E, beta-carotene, allopurinol, carvediol, and coenzyme Q.

12. The method of claim 10, which further comprises administering to the tissue at least one supplementary compound selected from the group consisting of corticosteroids, glucocorticoids, cyclooxygenase (COX) inhibitors, analgesics, substance P inhibitors, vanilloid receptor inhibitors, and other non-steroidal anti-inflammatory agents.

13. A method of inducing apoptosis and decreasing necrosis of pancreatic tissue in a subject diagnosed with pancreatitis comprising administering to said subject a curcumin compound having the following structural formula

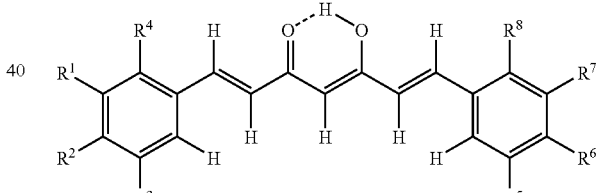

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

14. The method of claim 13, which further comprises administering to the subject at least one reactive oxygen species (ROS) inhibitor selected from the group consisting of N-acetylcysteine, vitamins C, A and E, beta-carotene, allopurinol, carvediol, and coenzyme Q.

15. The method of claim 13, which further comprises administering to the subject at least one supplementary compound selected from the group consisting of corticosteroids, glucocorticoids, cyclooxygenase (COX) inhibitors, analgesics, substance P inhibitors, vanilloid receptor inhibitors, and other non-steroidal anti-inflammatory agents.

16. A method of inhibiting AP-1 activation, NF-κB activation, trypsin activation, or neutrophil infiltration, in pancreatic tissue in a subject diagnosed with pancreatitis comprising administering to said subject a curcumin compound having the following structural formula

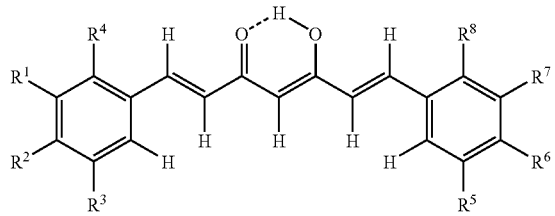

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

17. The method of claim 16, which further comprises administering to the tissue at least one reactive oxygen species (ROS) inhibitor selected from the group consisting of N-acetylcysteine, vitamins C, A and E, beta-carotene, allopurinol, carvediol, and coenzyme Q.

18. A method of activating or increasing caspase activity in pancreatic tissue in a subject diagnosed with pancreatitis comprising administering to said subject a curcumin compound having the following structural formula

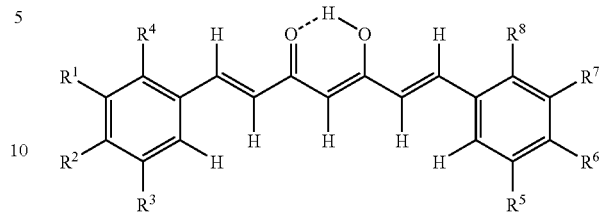

wherein $R^1$ to $R^6$ are each independently hydrogen, $NO_2$, alkyl, alkoxyl, acyl, hydroxyl, amino, alkylamino, dialkylamino, alkoxyl, carboxyl, or carbamoyl.

19. The method of claim 18, which further comprises administering to the tissue at least one reactive oxygen species (ROS) inhibitor selected from the group consisting of N-acetylcysteine, vitamins C, A and E, beta-carotene, allopurinol, carvediol, and coenzyme Q.

* * * * *

```
                        SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide probe containing a consensus kB
      binding site.

<400> SEQUENCE: 1
gcagagggga ctttccgaga                                              20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide probe containing phorbol ester
      responsive element .

<400> SEQUENCE: 2
ggcttgatga gtcagccgga a                                            21

<210> SEQ ID NO 3
<211> LENGTH: 21
<212> TYPE: DNA
<213> ORGANISM: Rattus sp.

<400> SEQUENCE: 3
caagagactt ccagccagtt g                                            21

<210> SEQ ID NO 4
<211> LENGTH: 22
<212> TYPE: DNA
<213> ORGANISM: Rattus sp.

<400> SEQUENCE: 4
gccgagtaga cctcatagtg ac                                           22

<210> SEQ ID NO 5
<211> LENGTH: 22
<212> TYPE: DNA
```

<213> ORGANISM: Rattus sp.

<400> SEQUENCE: 5
tgtgttccac caggagatgt tg          22

<210> SEQ ID NO 6
<211> LENGTH: 23
<212> TYPE: DNA
<213> ORGANISM: Rattus sp.

<400> SEQUENCE: 6
cagtttctgg tcgatgtcat gag          23

<210> SEQ ID NO 7
<211> LENGTH: 21
<212> TYPE: DNA
<213> ORGANISM: Rattus sp.

<400> SEQUENCE: 7
tgaacttcgg ggtgatcggt c          21

<210> SEQ ID NO 8
<211> LENGTH: 22
<212> TYPE: DNA
<213> ORGANISM: Rattus sp.

<400> SEQUENCE: 8
agccttgtcc cttgaagaga ac          22

<210> SEQ ID NO 9
<211> LENGTH: 22
<212> TYPE: DNA
<213> ORGANISM: Rattus sp.

<400> SEQUENCE: 9
cactatgcag gtctctgtca cg          22

<210> SEQ ID NO 10
<211> LENGTH: 22
<212> TYPE: DNA
<213> ORGANISM: Rattus sp.

<400> SEQUENCE: 10
gatctcactt ggttctggtc ca          22

<210> SEQ ID NO 11
<211> LENGTH: 21
<212> TYPE: DNA
<213> ORGANISM: Rattus sp.

<400> SEQUENCE: 11
cagtgagctg cgctgtccaa t          21

<210> SEQ ID NO 12
<211> LENGTH: 23
<212> TYPE: DNA
<213> ORGANISM: Rattus sp.

<400> SEQUENCE: 12
cagttagcct tgcctttgtt cag          23

<210> SEQ ID NO 13
<211> LENGTH: 21

```
<212> TYPE: DNA
<213> ORGANISM: Rattus sp.

<400> SEQUENCE: 13
gttgaacatc tccccttct c                                              21

<210> SEQ ID NO 14
<211> LENGTH: 21
<212> TYPE: DNA
<213> ORGANISM: Rattus sp.

<400> SEQUENCE: 14
atgtcctcat cggattcctc c                                             21

<210> SEQ ID NO 15
<211> LENGTH: 21
<212> TYPE: DNA
<213> ORGANISM: Rattus sp.

<400> SEQUENCE: 15
caatgagctg cgctgtcagt g                                             21

<210> SEQ ID NO 16
<211> LENGTH: 22
<212> TYPE: DNA
<213> ORGANISM: Rattus sp.

<400> SEQUENCE: 16
cttggggaca ccctttagca tc                                            22

<210> SEQ ID NO 17
<211> LENGTH: 22
<212> TYPE: DNA
<213> ORGANISM: Rattus sp.

<400> SEQUENCE: 17
gggttggaga ctaactggat ga                                            22

<210> SEQ ID NO 18
<211> LENGTH: 20
<212> TYPE: DNA
<213> ORGANISM: Rattus sp.

<400> SEQUENCE: 18
ggatcgagct ccactcgctc                                               20
```